(12) United States Patent
Lee

(10) Patent No.: US 11,204,349 B1
(45) Date of Patent: Dec. 21, 2021

(54) METHODS AND COMPOSITIONS FOR POLYMER SUPERPARAMAGNETIC PARTICLES FOR NUCLEIC ACID EXTRACTION

(71) Applicant: Theranos IP Company, LLC, Healdsburg, CA (US)

(72) Inventor: Alex Ho Fai Lee, Fremont, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 166 days.

(21) Appl. No.: 16/172,638

(22) Filed: Oct. 26, 2018

Related U.S. Application Data

(60) Provisional application No. 62/577,680, filed on Oct. 26, 2017.

(51) Int. Cl.
*G01N 33/543* (2006.01)
*C12N 15/10* (2006.01)

(52) U.S. Cl.
CPC ..... *G01N 33/5434* (2013.01); *C12N 15/1013* (2013.01)

(58) Field of Classification Search
CPC .......................... G01N 33/5434; C12N 15/1013
See application file for complete search history.

(56) References Cited

PUBLICATIONS

Nguyen et al. Monodispersed polymer encapsulated superparamagnetic iron oxide nanoparticles for cell labeling. Polymer 2016, vol. 106, pp. 238-248. (Year: 2016).*
Wang et al. Preparation of monodisperse cross-linked PS-DVB-GMA-amino-Fe3O4 magnetic microspheres with Cu(II) ions removal property. J. Polym Res 2016 (published online Dec. 14, 2015) vol. 26, No. 6., pp. 1-10. (Year: 2016).*
Hou et al. Synthesis and application of streptavidin functionalized organosilica microparticles. J. Appl. Polym. Sci. 2015 (published online Oct. 21, 2014), vol. 132, Issue 9. pp. 1-10 (Year: 2015).*

* cited by examiner

*Primary Examiner* — Shafiqul Haq

(57) ABSTRACT

A composition is described comprising superparamagnetic particles. Optionally, the particles comprise microbeads. Optionally, the particles comprise nanobeads. Optionally, the particles are non-spherical particles. Optionally, the particles are non-spherical particles suitable for RNA or DNA extraction. A method is described for forming microparticles. Optionally, the method comprises using citrate precipitation. Optionally, a kit comprising one or more of the particles is described. Optionally, a kit for sample preparation for nucleic acid extraction is described comprising non-spherical microparticles or nanoparticles.

3 Claims, 22 Drawing Sheets

Batch no                1608040
Expiry date             2017-08

Volume                  10 mL, 100 mL
Conc. of beads          10 mg/mL
Storage                 Store at 2 °C to 8 °C
Cautions                None

QUALITY CONTROL         SPECIFICATIONS                              RESULTS

Functional Assay        Tested for free biotin binding capacity     756 pmoles/mg
AM-00017                Using $^{14}$C-conjugated biotin
                        Criterion: 650-900 pmoles free
                        Biotin bound per mg coated beads

US 11,204,349 B1

METHODS AND COMPOSITIONS FOR POLYMER SUPERPARAMAGNETIC PARTICLES FOR NUCLEIC ACID EXTRACTION

CROSS-REFERENCE TO RELATED APPLICATION

This application claims priority to U.S. Provisional Application Ser. No. 62/577,680 filed Oct. 26, 2017 and fully incorporated herein by reference for all purposes.

BACKGROUND

Magnetic particles have received a great deal of attention in biological, medical, diagnostic and engineering areas. Unfortunately, manufacturing cost and complexity associated with use of such particles have been barriers to broader implementation.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2017 Theranos, Inc.

SUMMARY

The disadvantages associated with the prior art are overcome by embodiments described herein.

Magnetic nanoparticles or microparticles as disclosed herein are suitable for biological, medical, diagnostic and engineering areas, because of their magnetic properties, versatility in immunity separations, applications as MRI contrast agent, biosensor and the targeted drug delivery. Of particular interest are superparamagnetic particles constructed from materials such as but not limited to Iron (II, III) oxide ($Fe_3O_4$-magnetite).

Superparamagnetic particles constructed from Iron (II, III) oxide ($Fe_3O_4$-magnetite) has potential in binding, extraction and purification of biomolecules including RNA, DNA, proteins, enzymes and organic small molecules; they may be used as MRI contrast agents; and as carriers of biomarkers and drugs. The versatility of superparamagnetic particles derives from the combination of an iron oxide core (typically $Fe_3O_4$) with a variety of coating materials. When the particles are placed in a magnetic field, they develop a strong internal magnetization from exchange coupling of electrons. This allows their movement to be controlled by the external magnetic field. When the field is removed, particles are no longer magnetized and have no magnetic memory. However, $Fe_3O_4$ is readily oxidized to hematite ($Fe_2O_3$), changing its magnetism from superparamagnetic to ferromagnetic. To avoid oxidation and to protect the metal core, natural and synthetic polymers and silica have been employed to coat the magnetic particles. A wide range of chemical functional groups can be introduced on the coating surface to increase stability, wetting properties and binding flexibility for various applications. Chemical functionalization by amines, carboxylic acids, epoxy, and aldehydes is usually used to immobilize proteins, enzymes, RNA, DNA biomolecules on the surface via covalent linkages.

Other approaches have been developed because the use of ethanol and other solvents was not compatible with automated molecular diagnostic platforms.

In one embodiment described herein, a composition is provided comprising superparamagnetic particles. Optionally, the particles comprise microbeads. Optionally, the particles comprise nanobeads. Optionally, the particles are non-spherical particles. Optionally, the particles are non-spherical particles suitable for RNA or DNA extraction.

In another embodiment described herein, a method is provided for forming microparticles. Optionally, the method comprises using citrate precipitation.

In another embodiment described herein, a kit comprising one or more of the particles is provided. Optionally, a kit for sample preparation for nucleic acid extraction is provided comprising non-spherical microparticles or nanoparticles.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DESCRIPTION OF THE SPECIFIC EMBODIMENTS

Figure 1:
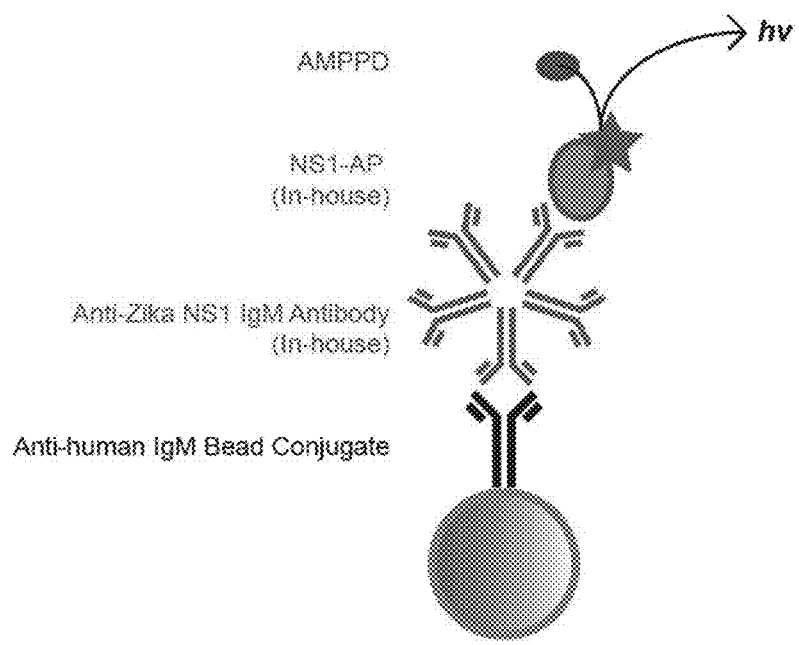
FIG. 1 shows one embodiment of a schematic of a Zika virus immunoassay.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µIL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

Materials & Methods

Described herein is the development of Streptavidin-conjugated superparamagnetic microparticles and it intermediates for immunoassay and biological materials separations.

In general, the superparamagnetic microparticles applications can be explained by the following example. The in-house developing ELISA assay which detects Zika IgM antibody in blood and cerebrospinal fluid (CSF).3 IgM antibody appears in blood a few days after Zika infection. A schematic of the ZIKV immunoassay is shown below in FIG. 1:

FIG. 1 Shows a Schematic of ZIKV Immunoassay

Streptavidin conjugated magnetic beads coated with biotinylated anti-human IgM antibody are incubated with serum or CSF. IgM antibodies in the blood bind to the beads, while unbound antibodies and serum components are removed by washing. Zika NS1 conjugated with alkaline phosphatase (Zika NS1-AP) is then added to the beads. Zika NS1-AP binds to human Zika-specific IgM antibodies and the amount of Zika NS1-AP bound to the beads are detected by using chemiluminescent substrate AMPPD.

The research and development of Streptavidin conjugated superparamagnetic microparticles and it intermediates are described. Those components are designed to be used as the magnetic separator or carrier for immunoassay and sample preparation purposes. Those usages included but not limited to (i) proteins, antibodies, antigens sample preparation and isolation. (ii) Cell separation. (iii) Protein-protein interaction studies. (iv) Immunoprecipitation. (v) Nucleic acid isolation and related sample preparation for PCR. (vi) IVD assay development. This document is intended to summarize and record the following aspects of the development.

Selection of the right polymers for the core assembly of microparticles.

Efforts to attain right size of monodispersed polymer spheres which is close to 2.8 µm diameter. This size is comparable to Dynabeads® M280 streptavidin-coupled.

Methods to introduce rigidity and chemical stability of the polymer particles to make them long shelf life and chemically inert for assay developments, robust in handling and stable in storage.

Efforts and ways to achieve the superparamagnetic properties of polymer microparticles by incorporating superparamagnetic iron (II, III) oxides, $Fe_3O_4$.

Functionalize the superparamagnetic polymer microparticles surface for conjugation purposes.

Streptavidin conjugation on the microparticles to assemble Streptavidin surface magnetic beads as the Final product for in-house applications.

Process development for the routine manufacturing which aimed to reduce batch to batch variability and provide more reliable and reproducible results for the purifications and analyses.

Pre-manufacturing verification and validation were done with MOP and MBR.

In-house development of superparamagnetic polymer microparticles are tube based concept. They are gentle and no columns or centrifugations are necessary. The true uniformity of bead size, shape and surface area should provide optimal accessibility and rapid liquid-phase reaction kinetics. In order to provide the insights for this characteristics, the quality control protocols are developed too.

The advantage and strength of the design for in-house superparamagnetic polymer microparticles are the concept of modular and ease of modification. This means the core, magnetic components, surface functionality and surface proteins, antibodies conjugation could be altered or modified without starting over from the beginning. These features could attribute to shorter research and product development cycles and faster turnover time with optimized cost effectiveness.

DEFINITIONS

Term Definition

St Styrene monomer
AIBN 2,2'-azobis(2-methylpropionitrile)
EtOH Ethanol or anhydrous ethanol
PAC Polyacrylic acid
Ar Argon inert gas
RCF Centrifuge Speed×g
DVB Divinylbenzene
GMA Glycidyl methacrylate
RT Room temperature
EDA Ethylene diamine
$FeCl_2 \cdot 4H_2O$ Iron (II) chloride tetrahydrate
$FeCl_3 \cdot 6H_2O$ Iron (III) chloride hexahydrate
NH3 Ammonium hydroxide
PS Polystyrene
PGMA Polyglycidyl methacrylate
NH2 Amine functional groups
Fe3O4 Iron (II, III) oxide, superparamagnetic
CHO Aldehyde functional groups
BSA Bovine Serum Albumin
SA Streptavidin
NaN3 Sodium azide
RLU Relative light units
QCP Quality control protocol
ELISA Enzyme-linked immunosorbent assay.
MOP Manufacturing operating procedure
MBR Manufacturing batch record
PBST Phosphate buffer saline with Tween 20
Biot-FAM Biotin-Fluorescein
DMSO Dimethyl sulfoxide
AP Alkaline phosphatase
AMPPD Chemilluminescence 1,2-dioxetane substrate for alkaline phosphatase

DISCUSSION

One embodiment of superparamagnetic polymer microparticles are designed to replace the commercial streptavidin-coupled beads. The present embodiment would open the new pathways for other superparamagnetic polymer microparticles applications, including separation and purification of biomolecules, MRI contrasting agent, biosensors and drug target payload delivery.4

In order to incorporate the design for highest efficiency in product development cycles and faster turnover time with optimized cost saving, the concept of modular and ease of modification was implemented. This involves the ease of alteration and modification of the core, magnetic components, surface functionality and surface proteins, antibodies conjugation without starting over from the beginning.

Figure 2:
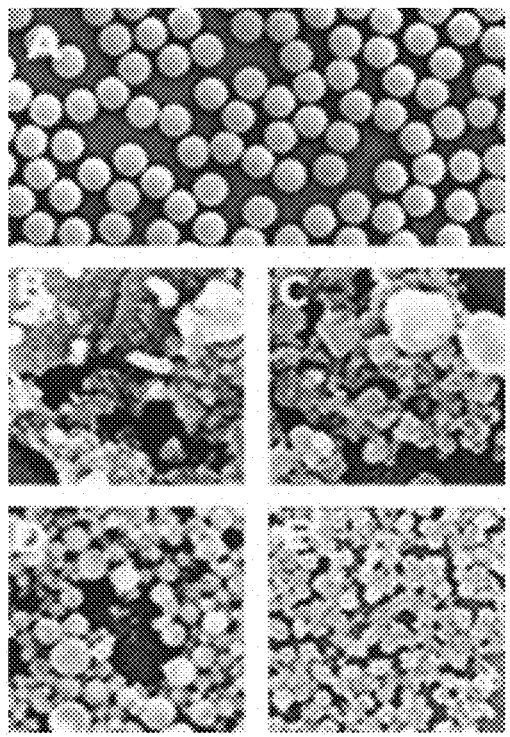
FIG. 2 shows SEM picture of magnetic particles.

One of the important features to make Dynabeads® products became to Gold Standard in superparamagnetic particles for Immunoassays development, separation and purification of biomolecules, is the uniform spherical and monodisperse stable particles. FIG. 2 below illustrates magnetic particles from alternative suppliers often have a random size range and surface area that could compromise the reproducibility of experimental results.

If superparamagnetic particles production could be tightly controlled and yield the uniform spherical beads, with highly defined and consistent product characteristics. These would reducing particle variability, and getting more reliable and reproducible results. Also, this would reduce the batch-to-batch variable and enhance the robustness of the whole process.

FIG. 2 shows SEM-pictures of Dynabeads (A) and alternative magnetic particles from other suppliers (B-E).

Figures 3, 4A:
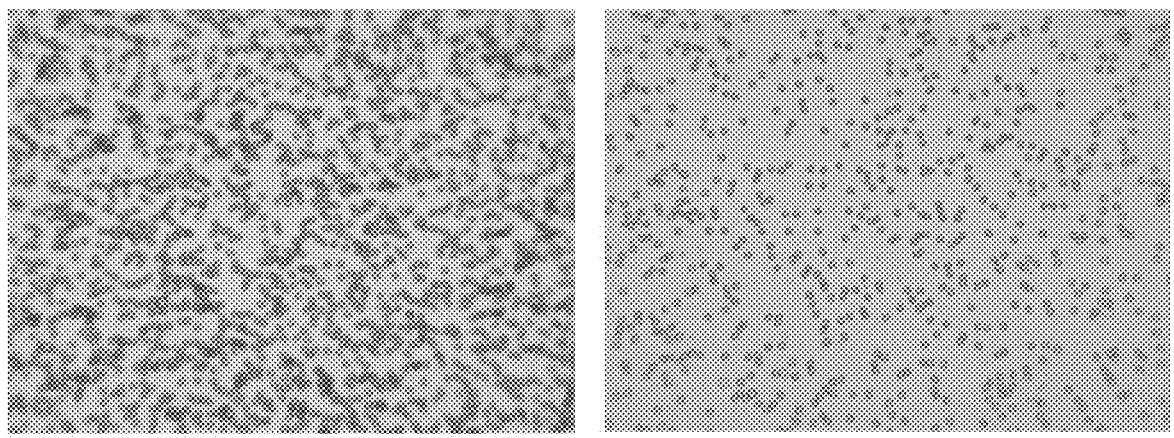
FIG. 3 shows specifications for magnetic particles.
FIG. 4A shows images of magnetic beads.

The development of the one embodiment of superparamagnetic particles design input and specification be based in part on the specifications of Dynabeads® M280 Streptavidin beads. FIG. 3 below is an example of a batch of Dynabeads®.

FIG. 3 shows Dynabeads specifications.

QCP were narrowed down to (i) Biotin Loading, (ii) Size analysis by Beckman Coulter Z2 Particle Counter with 50 μm aperature. Microscopic Imaging were served as in process QC. FIG. 4 below showing the comparison of Dynabeads M280 SA beads and in-house developed SA beads with same magnification.

FIG. 4A shows Dynabeads M280 SA beads (right) and in-house developed SA beads (left) with same magnification.

One Embodiment of the Procedure

One Embodiment of Overall Pathway of Multistep Synthesis

Figure 4B:
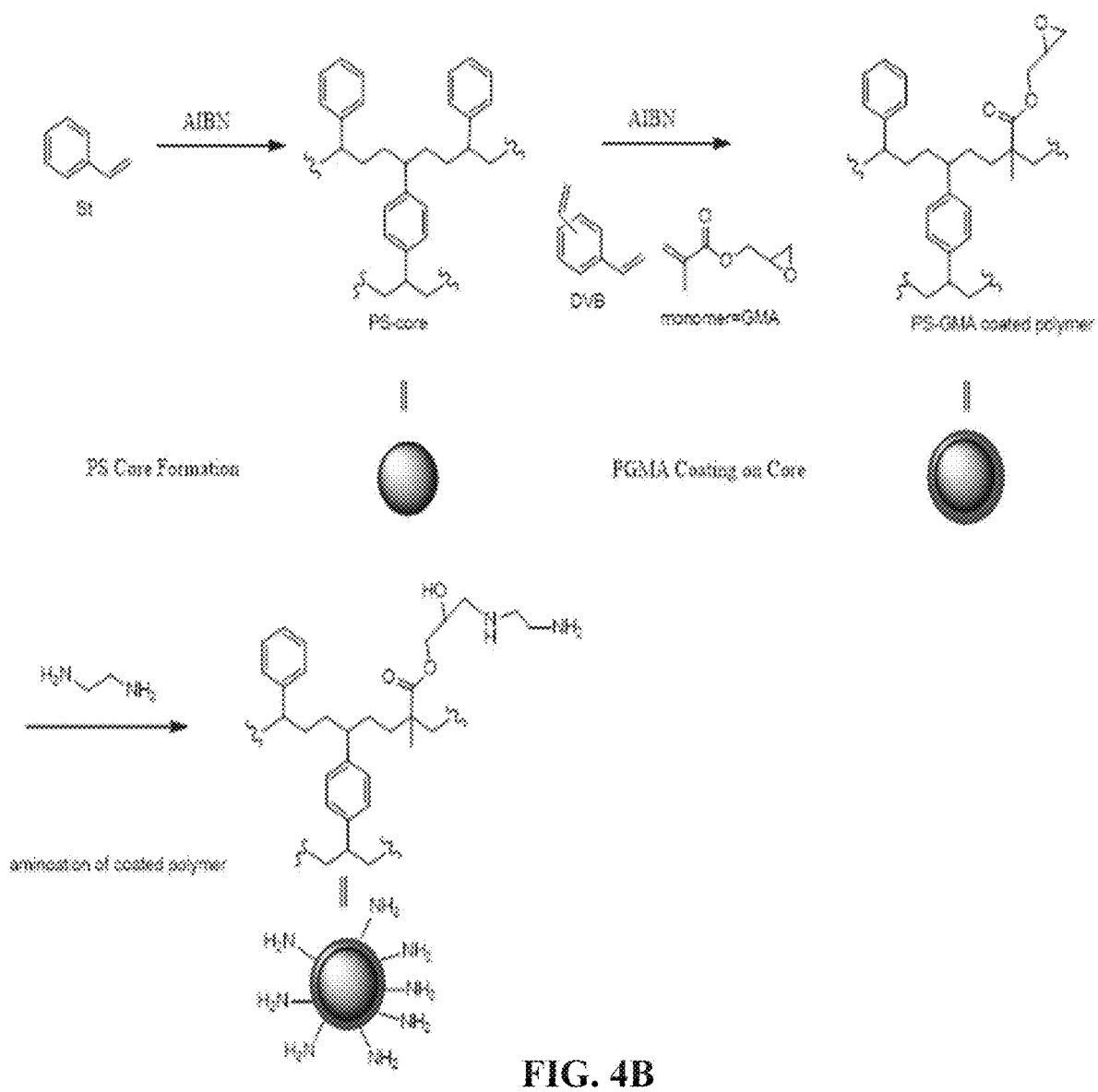
FIGS. 4B-4D show embodiments of synthesis techniques.
Figure 4C:
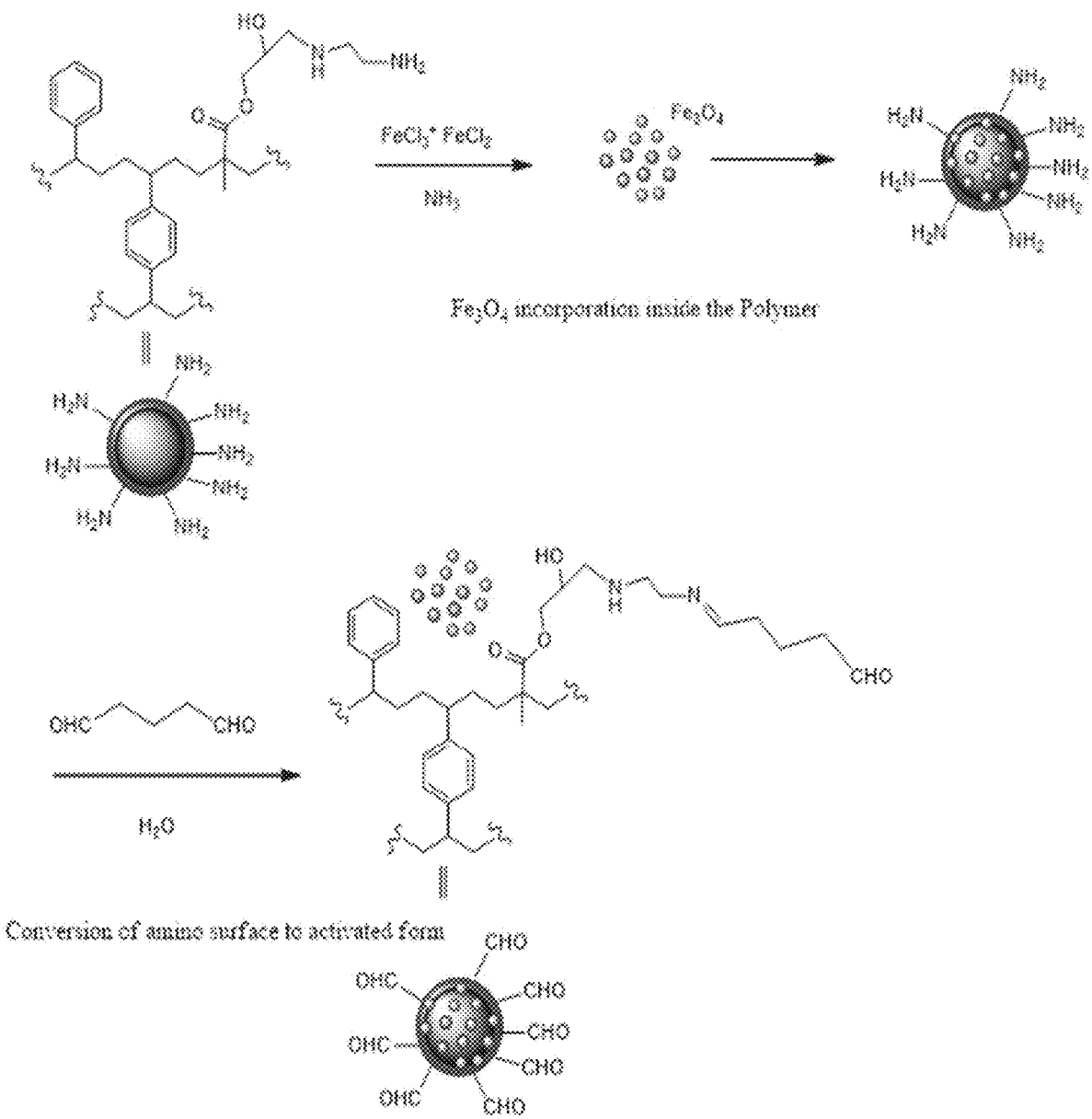
Figure 4D:
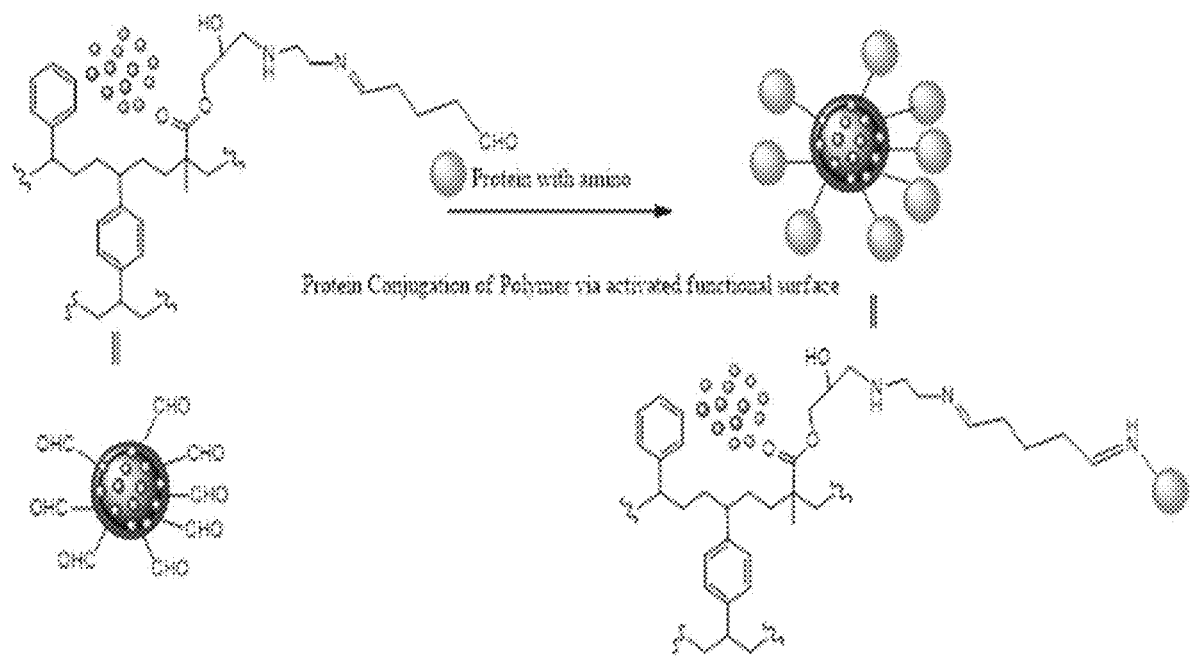

See FIG. 4B for Scheme 1 comprising: Steps (1) Polymerization of Core→(2) Coating of Core→(3) Amination of Coating See FIG. 4C for Scheme 2 comprising Steps (4) Iron(II, III) oxide Incorporation→(5) Surface activation from amino to aldehyde See FIG. 4D for Scheme 3 comprising: Steps (6) Protein Conjugation via amino groups of protein with aldehyde of beads The 3 schemes above showing the (1) core formation with special type of polymerization with styrene monomer. (2) PGMA coating on the PS seeds. (3) Amination of the epoxy function groups from PGMA coating. (4) Fe3O4 superparamagnetic nanoparticles incorporation inside the polymer microparticles. (5) Aldehyde functionalization with glutaraldehyde. (6) Final Streptavidin as a protein to conjugate to the surface aldehyde.

6.3 In this non-limiting example, the first step of the whole synthetic pathway for synthesis of in-house superparamagnetic microparticles was proved to be very critical in both design and implementation. Because of this, a lot of other conditions and strategies had been tried out in order to narrow down and finalize to this condition. The condition records below is the seeding method which can ensure the right size and highly monodispersed PS seeds to be prepared. For pre-manufacture synthesis, a 2 Liter jacketed reactor equipped with overhead stirrer have been selected. (FIG. 5)

Figure 5:
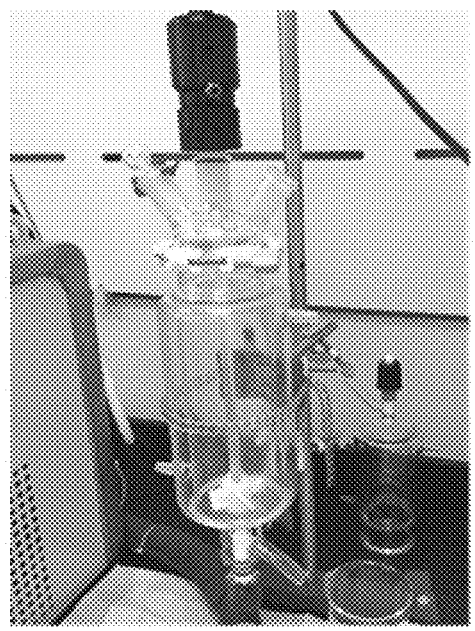
FIG. 5 shows a liter jacketed reactor.

FIG. 5 shows one embodiment of a 2 Liter jacketed reactor equipped with overhead stirrer for Seeds polymerization in Step 1.

The following table summarizes the component of the reagents needed to start the optimized polymerization for PS core seeds. The manufacturing operating procedure was recorded in MOP-00807-F1.6 All of the reagents were dissolved in the ethanol-water mixture and purged with Ar in the reactor. The overhead stirrer was set to 500 rpm and circulator temperature of the jacket was adjusted to about 70° C. The polymerizations were carried out for overnight. Once they are done, the reactor temperature was ramped down to room temperature and the contents were transfer from the reactor to centrifuge tubes. Centrifuge the material at 1500 rcf, and disposed of the supernatant, repeat the washing procedure with fresh ethanol for seven times.

| Item (Step1) | Amount (100 ml St) |
|---|---|
| St | 100 ml |
| AIBN | 0.89 g |
| EtOH anhyd ( 4L bottle EMD, EX0285-3 ) | 700 ml |
| DI water | 14 ml |
| PAC 450k Da | 1.04 g |

Purification or separation of the PS seeds was relied on the centrifuge. Once it was done, the seeds were dried in vacuum oven at 50 C with 30 in Hg vacuum pressure. In process microscopic images showing the uniform monodisperse particle with ~2.2 μm in reproducible manner for all the batches made.

Figure 6:
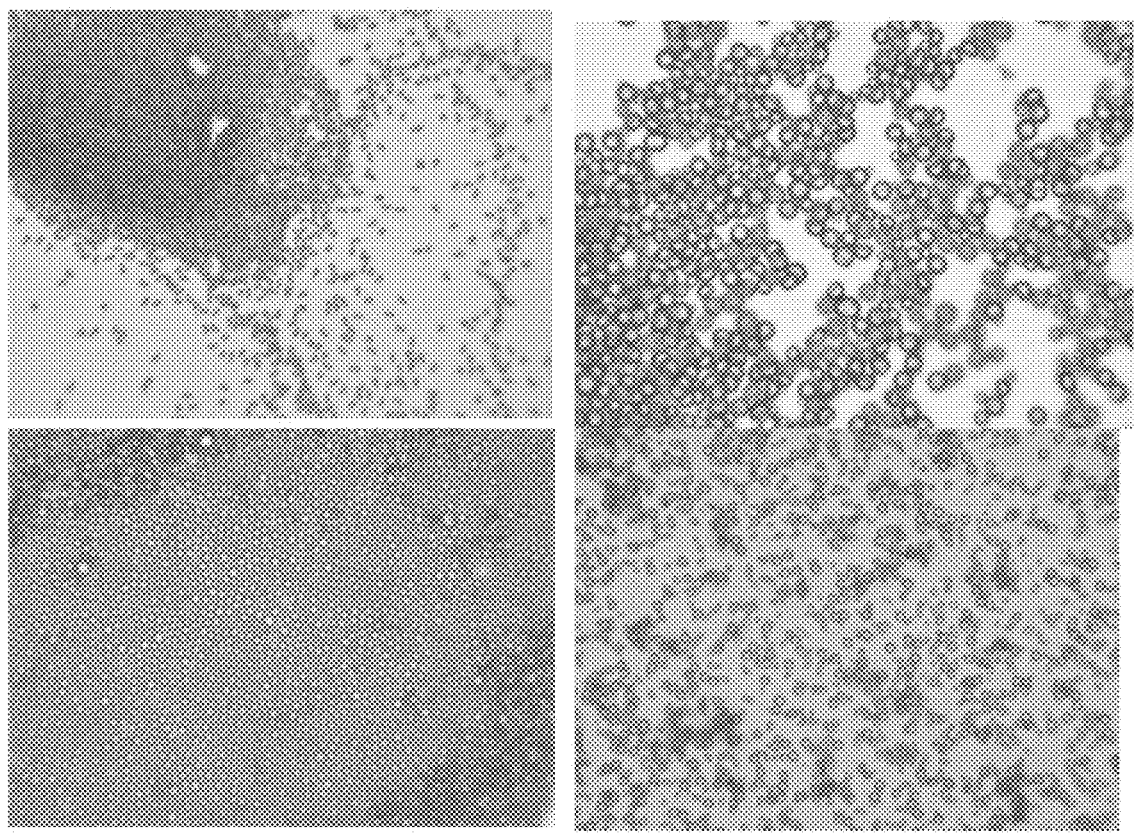
FIG. 6 shows co-polymerization particles microscopic images.

6.4 In this non-limiting example, the second step of the preparation is PGMA coating on the seeds. The following table summarizes the materials needed in this step. Seeding method was chosen rather than using styrene, DVB, and GMA co-polymerization at single step is because the previous experiments proved the monodispersion uniform spherical particles from polymerization were only achieved by seeding methods. FIG. 6 showing co-polymerization particles microscopic image with same 800× magnification. All of them were suffered by non-spherical shape, multiple sizes of the beads formed at the same polymerization batch or sizes are much larger than 2.8 μm.

| Item (Step2) | R&D procedure | Pre-manufacture procedure |
|---|---|---|
| PS Seed | 0.5 g | 5 g |
| St | 0 | 0 |
| DVB | 25 ul | 0.25 ml |
| GMA | 0.5 ml | 5 ml |
| AIBN | 15 mg | 150 mg |
| EtOH anhyd | 16 ml + 2 ml GMA/ EtOH adsorption 1 h | 160 + 20 |
| DI water | 1 ml | 25 ml |
| PAC 450k Da | 30 mg | 400 mg |

FIG. 6 shows co-polymerization particles microscopic images with same 800× magnification.

Therefore, coating of PGMA on the PS seeds recorded in the above table of materials was the optimized set of selection. Coating procedures were routinely done by pre-suspending PS seeds in ethanol-water mixture, followed with DVB, GMA, AIBN mixture in ethanol slowly dropwise addition to seeds suspension. After purging with Ar and stirring for an hour, the mixture was started heating with 120° C. hot plate setting, and internal temperature reached 80° C. The coating needed 6 h to complete. If the reaction time was not enough, the coating would not complete and the next couple steps would yield the bead suspension prone to be aggregation.

Once the reactions were done, the contents were cool down to room temperature and separated by centrifuge with 1000 rcf. The supernatant was disposed, and the beads were washed with fresh ethanol and repeat the separation with centrifuge at 1000 rcf for 5 times. The brief centrifugation served as the most convenient choices of purification in those processes, and this selection makes the processes readily scale up and enhance the speed and low costs of the preparations. Moreover, the coating quality could be verified by the upcoming steps immediately. Once the PGMA coated beads were separated, they were subjected to next step directly without drying.

6.5 In this non-limiting example, the third step of the preparation is amination of the coated beads. Table below showing the materials in optimized amounts used in this reaction step. Largely excess of ethylene diame (EDA) was used to react with the epoxy functional groups on the PGMA coating. The condition was finely optimized and avoid the intermolecular reaction could be happened and causing aggregation of the beads. In general, coated beads were suspended in ethanol and the DEA in ethanol was added in one shot to the beads suspension. Stirring and sonication would be the best combination of agitation. Once the stirring of the reaction mixture was done by overnight at room temperature. The aminated surface beads were separated and washed with ethanol with the help of centrifuge at 2200 rcf. After 6 times of repeated washings, the beads were dried in vacuum oven as the description of related MOP00809-F1.8 In this and last step, the preparation were done on the 500 to 1000 ml Erlenemeryer flasks with screw cap for Ar purging capability, see FIG. 7.

Figure 7:
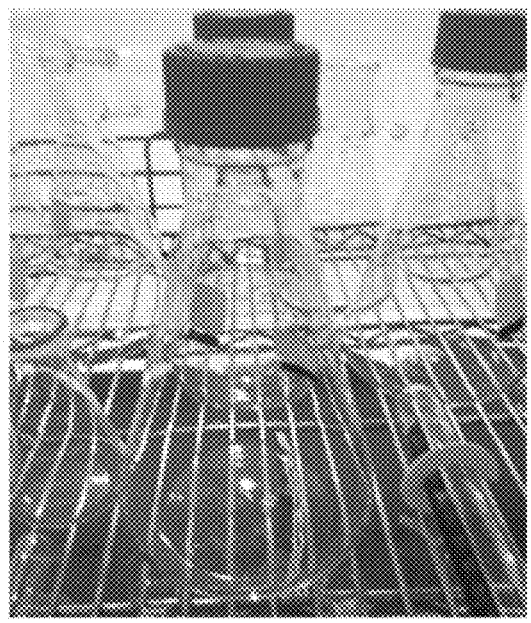
FIG. 7 shows Erlenemeryer flasks for coating and amination steps.

FIG. 7 shows one embodiment of Erlenemeryer flasks for coating and amination steps.

| Item (Step3) | 2.2 um Beads Amination |
|---|---|
| PGMA coated Seeds | 5 g |
| DEA | 12 ml in 36 ml EtOH |
| EtOH anhyd | 180 ml EtOH for PGMA seeds suspension |

Figure 8:
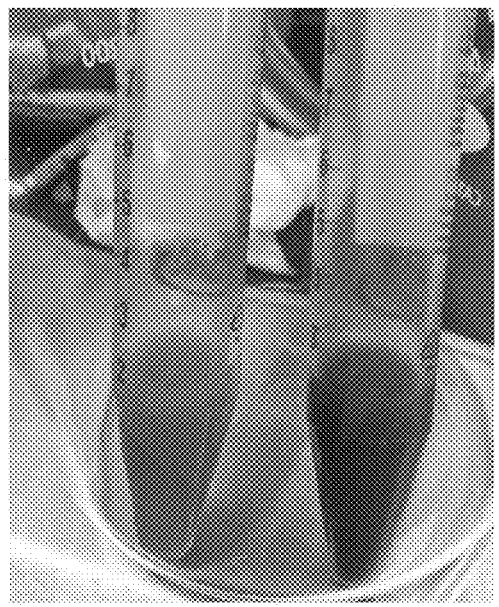
FIG. 8 shows test results.
Figure 9:
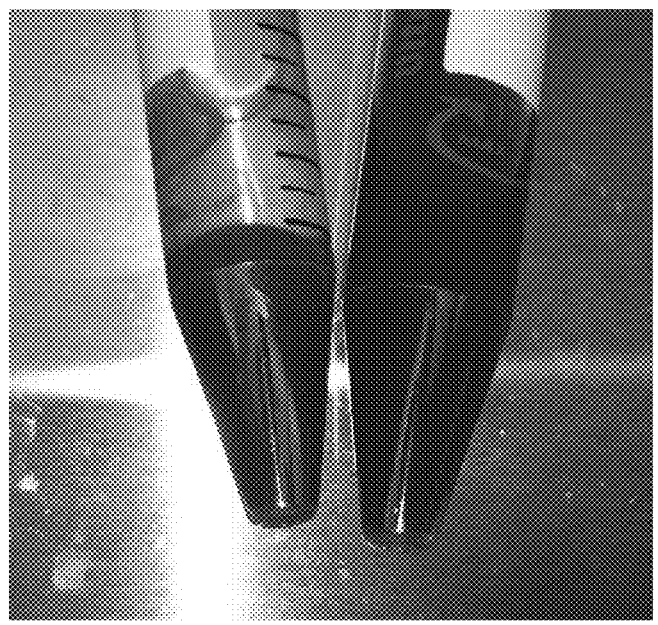
FIG. 9 shows color different Fe precipitation.

6.6 Iron oxide incorporation step is the one to make the polymer microparticles become superparamagnetic. Many different approaches had been tried out in order to get the superparamagnetic nanoparticles of Iron (II, III) oxides ($Fe_3O_4$) entrapped inside the polymers. Following FIG. 8 illustrates the comparison of the two major methods used. Which is (1) swelling and entrapping and (2) precipitation methods. At the end, the precipitation was selected and optimized here for the preparation.9 Swelling and entrapping method was not able to bring enough amount of Fe inside the beads and which shown in the FIG. 8 with pale brown color verse brown color of precipitation method. Meanwhile, swelling method require using toluene as the solvent which require higher amount of DVB to keep the rigidity and chemical stability of the beads structure. Higher amount of DVB would cause the monodispersed uniform beads harder to form. Precipitation method used here was also able to yield different loading of the Fe content and which was fine tuned to match the magnetic response in order to achieve similar performance under the same strength of magnets. FIG. 9 showing different loading of the Fe and the color changes.

FIG. 8 shows results of beads from swelling and entrapping (left), and precipitation (right) methods.

FIG. 9 shows color different of Fe precipitation 1× (left), and 2× ratio (right).

The following table summarizes the optimized amounts of the reagents used in Fe3O4 incorporation step. Higher Fe loading is not essentially to achieve the best performance as the deeper color would absorb the chemiluminescence radiation emitted by AMPPD substrate of AP.

| Item (Step4) | Fe(II, III) oxide in Amino Beads R&D | Pre-manufacture batches |
| --- | --- | --- |
| FeCl3·6H2O | 250 mg | 3.9 g |
| FeCl2·4H2O | 120 mg | 1.9 g |
| DI water for FeClx dissolution | 3 ml | 40 ml |
| NH3 | 3 ml | 47 ml |
| Amino Beads | 490 mg | 6.2 g |
| DI water for beads suspension | 15 ml | 190 ml |

Amination beads were first suspended in the deionized water, if the coating of PGMA was not complete, the beads starting material with amine surface would not enough to make them suspended well in aqueous. This important observation was serving as one of the in process QC, and which can stop the process moving forward by itself if the thing went wrong. This design is sophisticated as the amine surface is essential to provide the hydrophilic environment of the beads for the Fe2+, Fe3+ ions to penetrate the polymer surface. Meanwhile, the amine surface is required for the beads to well suspend in the aqueous for this step of reaction to go forward. Once the Fe ions go inside the beads, ammonia added will start precipitate the Fe ions to form Fe3O4 nanoparticles. These particles trap inside the polymer makes this preparation complete.

| Item (Step5) | Surface activation of 2.2 um Fe(II, III) oxide incorp Beads |
| --- | --- |
| Fe(II,III) Oxide incorp Beads | 1 g |
| 50% Glutaraldehyde | 3.5 ml |
| DI water | 28 ml |

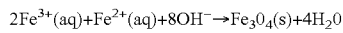

In general, the procedure was carried out by suspending amine surface beads in the deionized water as above ratio. Adding the beads suspension into the dissolved Fe2+, Fe3+ solution, and stirred for 2 hours to allow the Fe ions penetration inside the polymer beads. Purging of the Ar was needed to avoid the other form of iron oxides formation. After stirring for 2 h, ammonia 28-30% w/w was added dropwise and the mixture was agitated with stirring and sonication alternatively. Once the addition was finished, the mixture was heated to 80° C. with hotplate set to 130° C. and stirred for 2.5 h. At the end, the content was cool down to room temperature and the Iron (II, III) oxide incorporated beads were washes with deionized water and separated with centrifuge at 2500 rcf for 10 to 15 times until no color supernatant remained. Magnetic separation could be served as a replacement of centrifuge, however, the high throughput magnetic device is needed in order to achieve this grams-scale of preparation. In this step, the dried beads could be stored at freezer −18° C. for 52 weeks shelf life.

6.7 Aldehyde surface activated beads preparation was done by suspending the dried Fe3O4 incorporated beads and reacted with largely excess glutaraldehyde solution.10 Table below summarizes the optimized condition. For the planning of the streamlining manufacturing, 1.4-1.5 gram of the dried Fe3O4 incorporated beads could be stored in a 50 ml Falcon tube for each reaction, and this would be all the way carried down to last step: Streptavidin loading. (FIG. 10)

Figure 10:
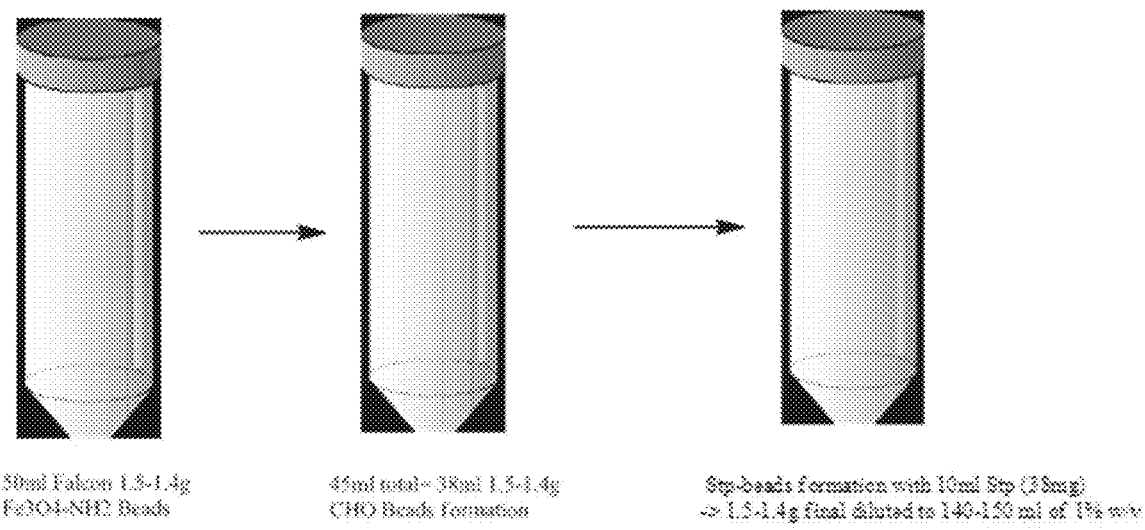
FIG. 10 shows aliquoted plans for the stockpile of beads intermediates.

FIG. 10 shows aliquoted plans for the stockpile of beads intermediates. Every tube of 50 ml Flacon tube can serve as a unit for the preparation all the way down to Streptavidin beads.

Once the reaction completed in 1.5 h, the aldehyde activated beads were washed with deionized water to remove excess glutaraldehyde. Again centrifuge at 2500 ref was used for the separation, and this set-up can ensure the best use of instrument and simplify the process. CHO beads could be subjected to next step without drying and the loss of the beads during separation is minimal.

6.8 Streptavidin conjugated beads were done by simply adding the right amount of Streptavidin into the deionized water suspended CHO activated particles. The design of this step was aimed to simplify the conjugation step and make it available for non-trained workers. CHO activated particles are stable and highly activate towards amines side chain of the proteins including streptavidin here. The control of the loading could be possible by adjust the level of protein addition. At the end, BSA was added for covalent binding to the rest of CHO groups or non-covalent binding to the surface of protein. Final formulation was kept as 1% w/v of beads in deionized water with 0.02% NaN3 as an anti-microbial additive. Following table indicated the R&D and pre-manufacturing phase condition of this step. Process development and pre-manufacturing condition increase amount of Streptavidin used in order to maximum the loading and driving the kinetic forward.

Figure 11:
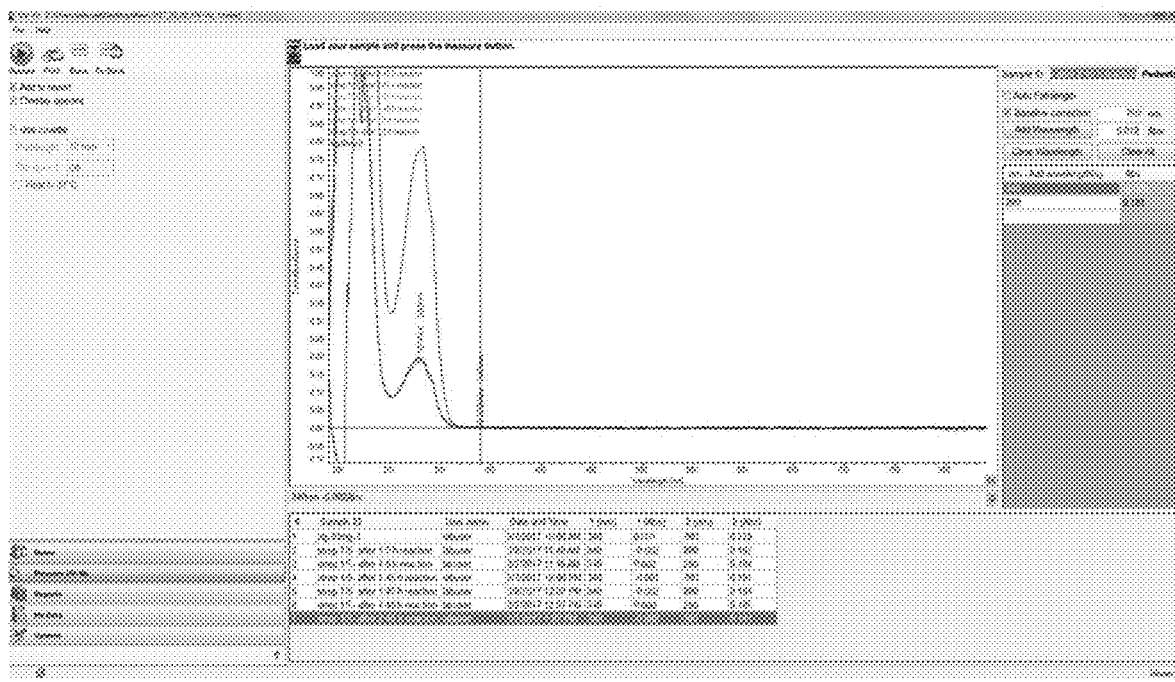
FIG. 11 shows signal results.

FIG. 11 is the nanodrop UV-Vis illustrate the initial and final A280 signal from free streptavidin in the solution.

| Item (Step6) | Streptavidin Conjuagtion of 2.2 um surface activated beads (R&D) | Pre-manufacturing |
| --- | --- | --- |
| Beads | 150 mg | 1 g |
| Streptavidin | 1.36 mg | 33.3 mg |
| DI water | 3 ml (for beads) + 1 ml (for Streptavidin) | 29 ml + 5 ml |
| 5% BSA in 1xPBS | 200 ul | 570 ul |

FIG. 11 shows nanodrop UV-Vis illustrate the initial and final A280 signal from free streptavidin in the solution.

When 33.3 mg of Streptavidin lyophilized powder was weighed out and dissolved in 5 ml of deionized water, A280 was measured as 0.868 by 2 fold dilution. Which is equal to 5.43 mg/ml. 4 ml of 5.43 mg·ml Streptavidin solution added makes up 21.75 mg initial. No buffer is needed because the lyophilized protein comes with salt there. FIG. 11 indicates final A280 remained essentially the same after 1 h 45 min.

Verification and Validation

Figure 12:
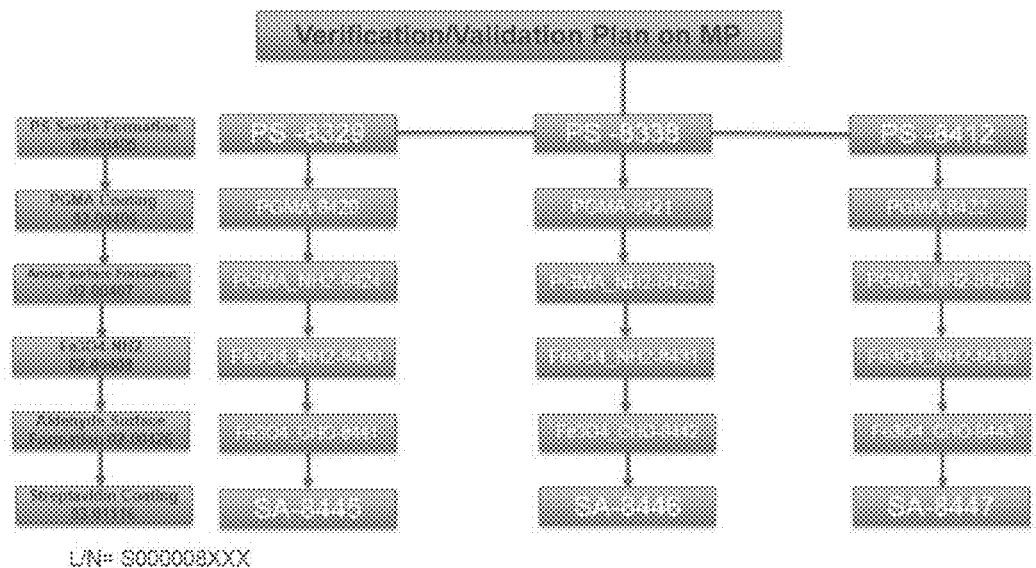
FIGS. 12-15 shows data from various batches.

Verification and validation of the preparation process were done in pre-manufacturing phase with MOP and MBR of each step ready. The following FIG. 12 illustrates the diagram of the first triplicate batches all the way from 3 separated batches of Starting PS seeds carried down parallel to the final SA-beads. The microscopic images were recorded and compared to the previous format of process development done by Adam Mann (A Senior Scientist who failed in the process development of this project for 2 years).12 The new processes described here demonstrate every step of intermediates behave much closer to R&D results. Monodisperses and uniformity of beads are greatly improved when compare the Images (Microscope 800×) from FIG. 13 (Current Process Development described here) and FIG. 14 (Previous Failure of the process done by another scientist in past 2 years) for every step.

Figure 15:
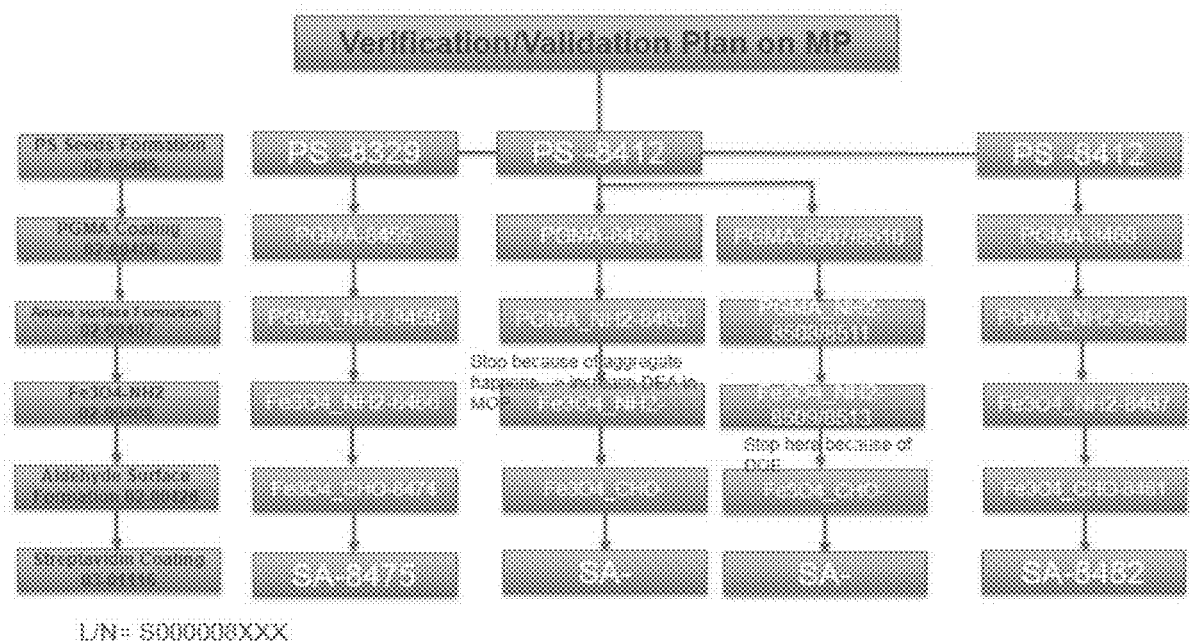

FIG. 15 shows more batches done with L/N for verification and validation.

FIG. 15 recorded the S000008460 batch ended up with aggregation. This finding was finally resolved by using another lot number of GMA reagent from Sigma Aldrich used to prepare PGMA coating step. Original L/N MKBT8176V proved to be not as good as MKCB8502 from the vender. Although the same L/N of reagent has been used before, however, they are from different bottles and opened at different time. Besides, amount of water used in PGMA coating step was further adjusted in order to improve the result. Following table showing the adjustment of couple of parameters and conditions to make sure the reproducibility of the processes. S000008509 and S000008511 were 2 batches of Fe3O4 incorporated beads stockpiled here for later usage.

| P/N | Name | Condition A | Condition B | Condition C | Best |
| --- | --- | --- | --- | --- | --- |
| 02-00406 | Coated beads | 1 h/2 h -> X | 1 h/4 h -> X | 1-1.5 h/5.5-6 h -> Good | C |
| 02-00406 | Coated beads | 20 ml water (5 g scale) -> ok | 25 ml water (5g scale) -> good | 0.5 ml water-> failed | B |
| 02-00407 | Amined | 1x diamine -> good | 1.5x diamine -> good | 1.2x diamine -> good | C |
| 02-00408 | Fe3O4-NH2 | 1 h/2 h -> good | 2 h/2.5 h -> good | 2 h/2 h -> good | C |
| 03-01116 | SA | 6 mg SA : 700 mg 02-00426 R&D phase) -> ok | 15 mg SA : 700 mg 02-00426 -> ok | 24 mg SA:700 mg -> ok | C (make sure highly loaded) |
| 03-01116 | SA | 0.003% NaN3 in DI water | 0.02% NaN3 in DI water | | B (shared w. Dyna spec) |

FIG. 12 shows triplicate batches done with L/N for verification and validation.

Figure 13A:
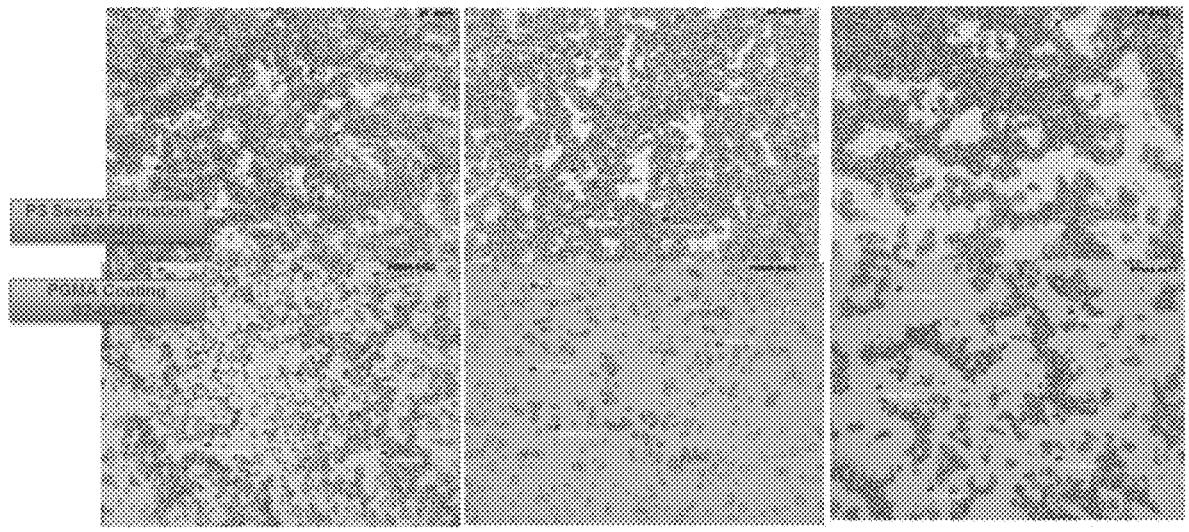
Figure 13B:
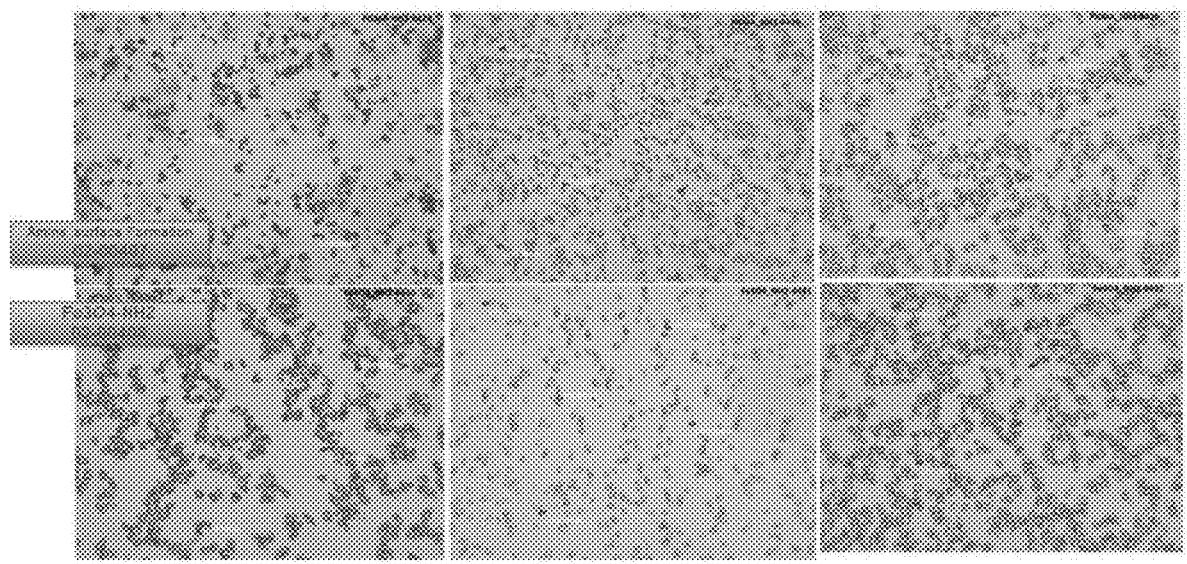
Figure 13C:
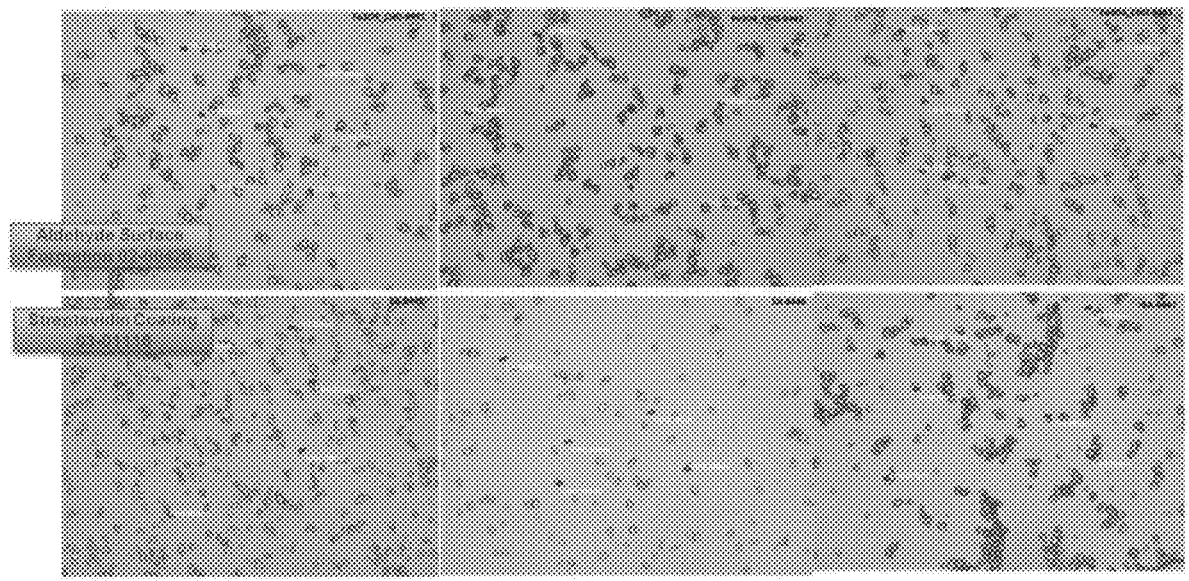

FIG. 13 shows triplicate batches done with L/N for verification and validation observed in microscopic image with 800× magnification.

Figure 14A:
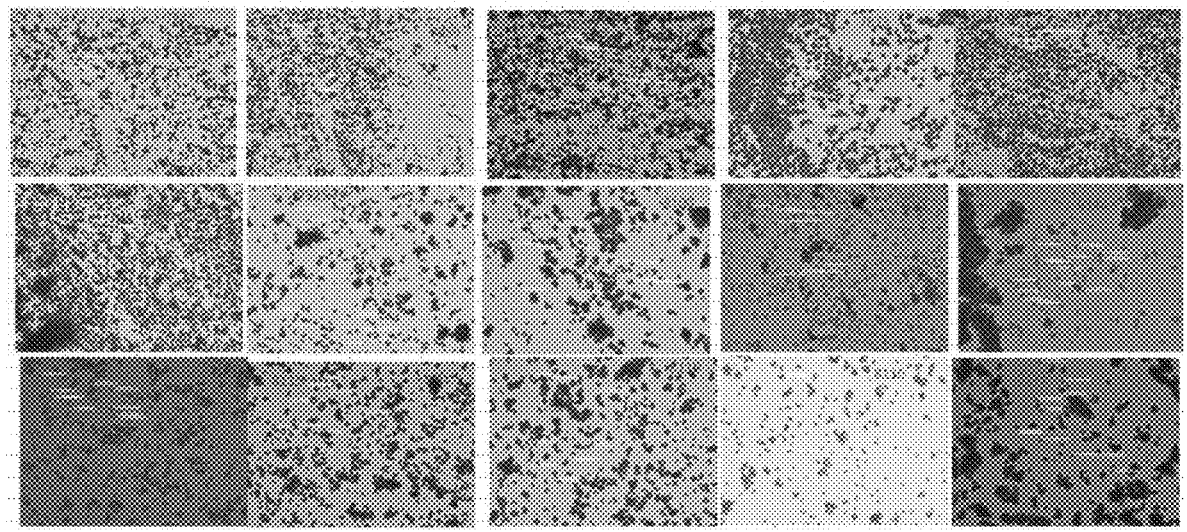
Figure 14B:
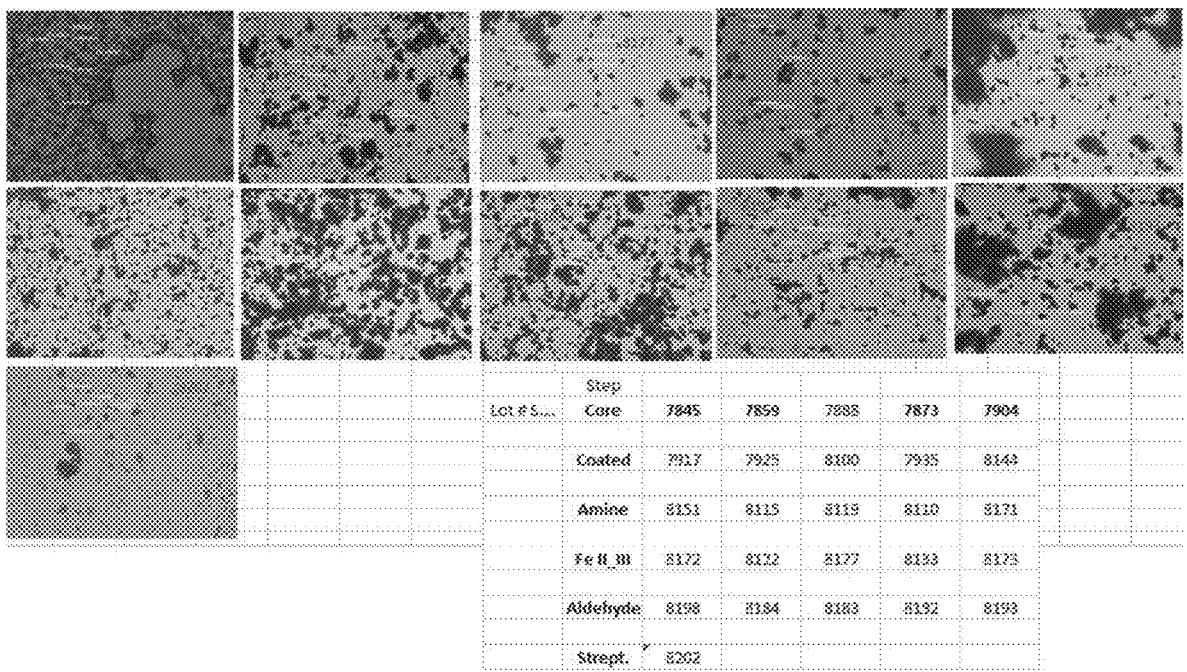

FIG. 14 shows previous process development batches done with L/N observed in microscopic image with 800× magnification.

Besides the triplicate verification and validation, the following FIG. 15 describes more batches were generated. The extra runs provided more information for the improvement of the processes and the tolerance of the conditions which is important to ensure the reproducibility and robustness of the preparations. Also, based on the collected data both in R&D and process re-development here, the shelf lives of the following items were extended. This could improve the overall effectiveness of the whole projects without compromising the quality of deliveries.

| P/N | 02-00405 | 02-00407 | 02-00408 |
| --- | --- | --- | --- |
| Product Name | Polystyrene Core Seeds | Aminated Coated Seeds | Iron (II, III) oxide Incorporated Beads |
| Previous shelf life | RT 25 W | RT 25 W | RT 20 W |
| Suggested change | RT 104 W | <4° C. 52 W | <4° C. 52 W |

In one non-limiting example, the method may comprise the following:

Step1: Forming polystyrene micron particle without crosslinker from styrene monomer (2 um).

Step2: Coating of polystyrene micron particles with PGMA (polyglycidyl methacrylate) layer and crosslinked with DVB (Divinylbenzene) (2.8 um) all the steps until last.

Step3: Amination of the epoxy surface from Step 2 product (PGMA layer)

Step4: Using the amine surface hydrophilicity to allow Ferric and Ferrous Chloride to penetrate inside the beads and forming precipitate that trapped inside the beads by reacting Ferric and Ferrous Chlordie with ammonia.

Step5: Using glutaraldehyde to react with amine surface and form the aldehyde activated surface for next step.

Step6: react aldehyde surface with protein lysine side chain (here is streptavidin in our product) to lead to streptavidin conjugated beads. (2.8 um)

8. Qualitative Analysis Development

Quality control of the in-house developed Streptavidin conjugated beads were done by 2 major protocols developed by the team based on the specification of Dynabeads® M280 SA beads.

Figure 16A:
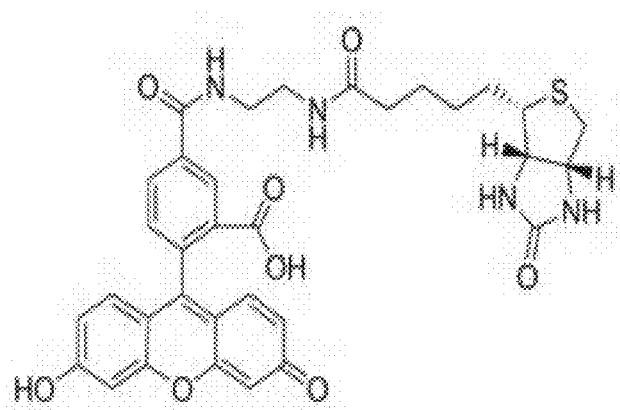
FIG. 16A shows chemical structure of Biot-FAM.
Figure 16B:
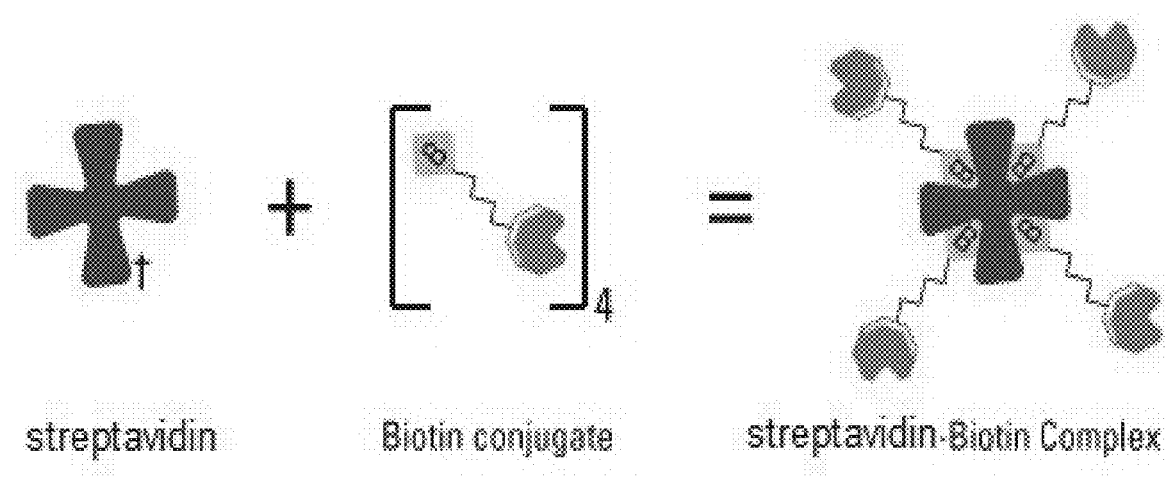
FIG. 16B shows a way of binding between Biot-FAM with Streptavidin.
Figure 16C:
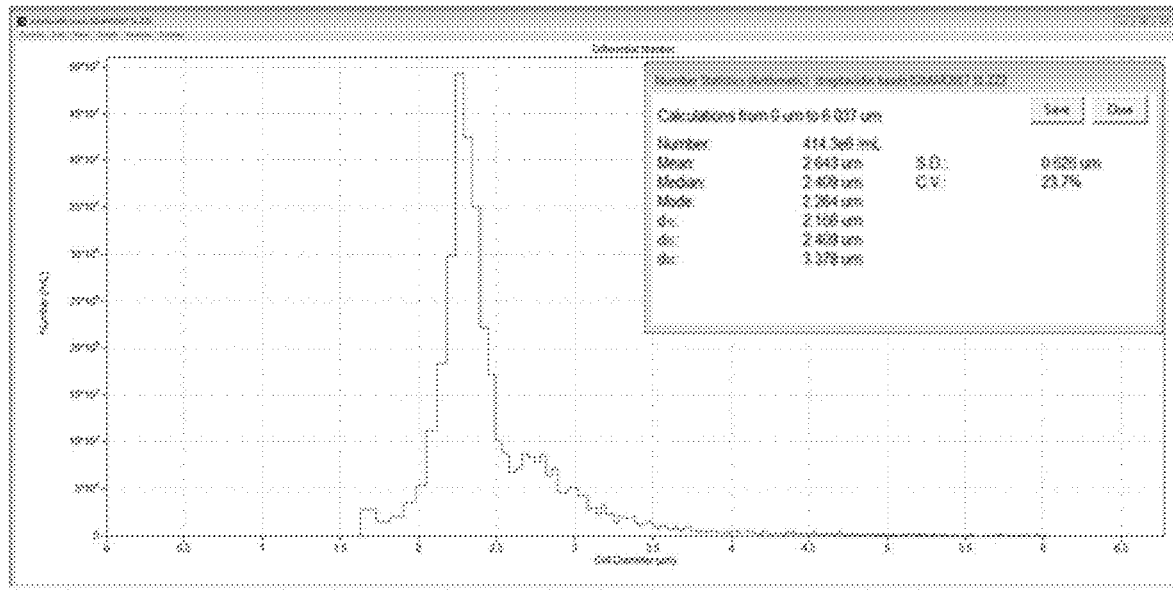
FIGS. 16C-16J shows data from various results.
Figure 16D:
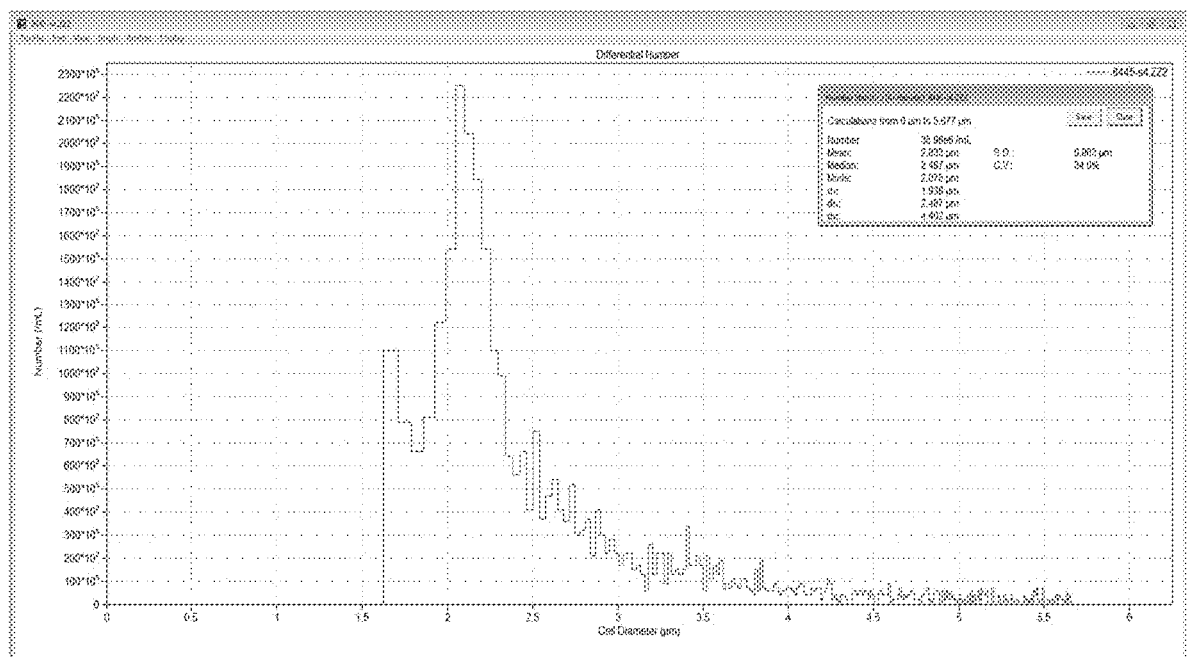
Figure 16E:
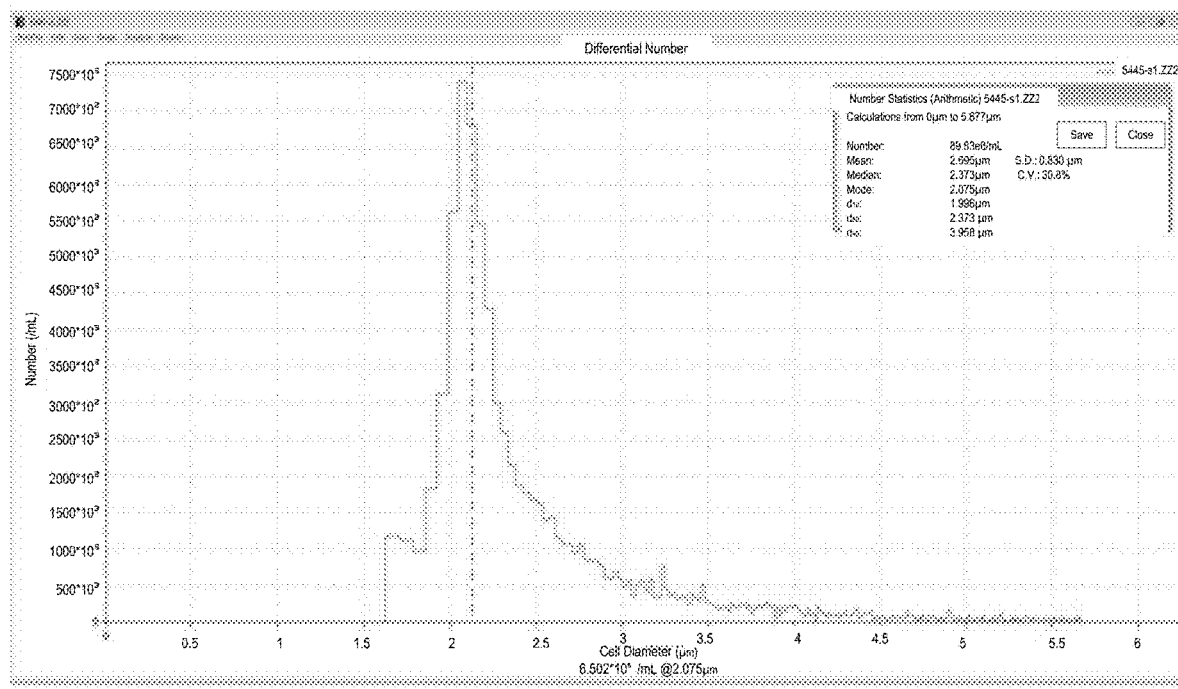
Figure 16F:
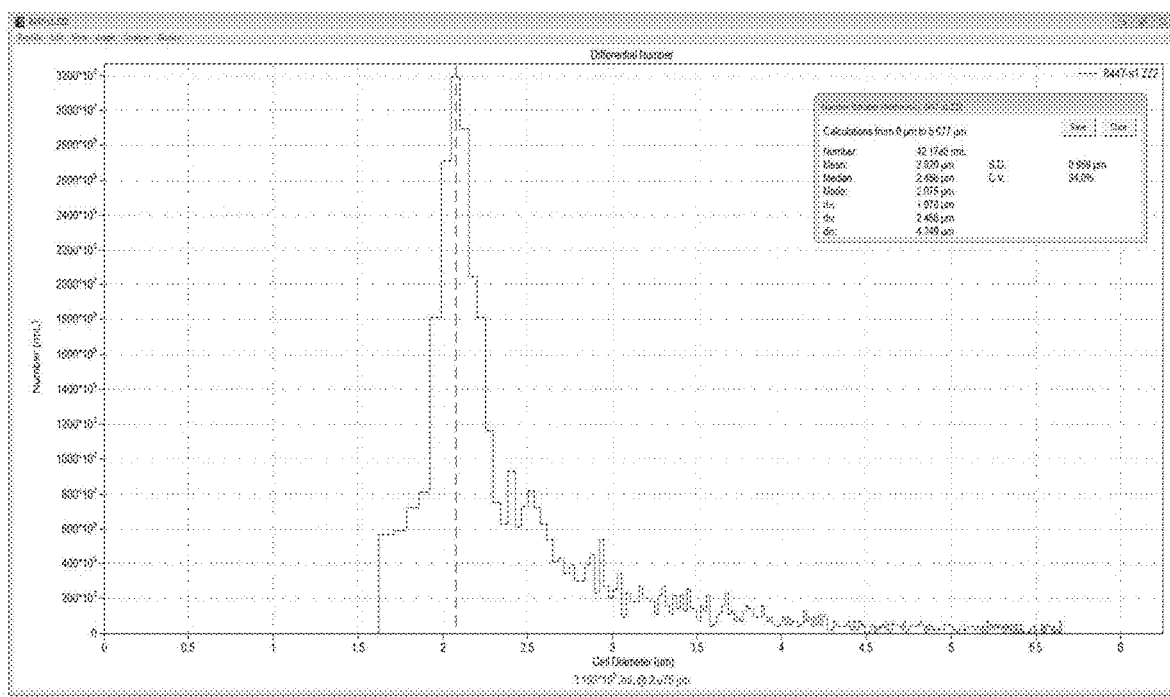
Figure 16G:
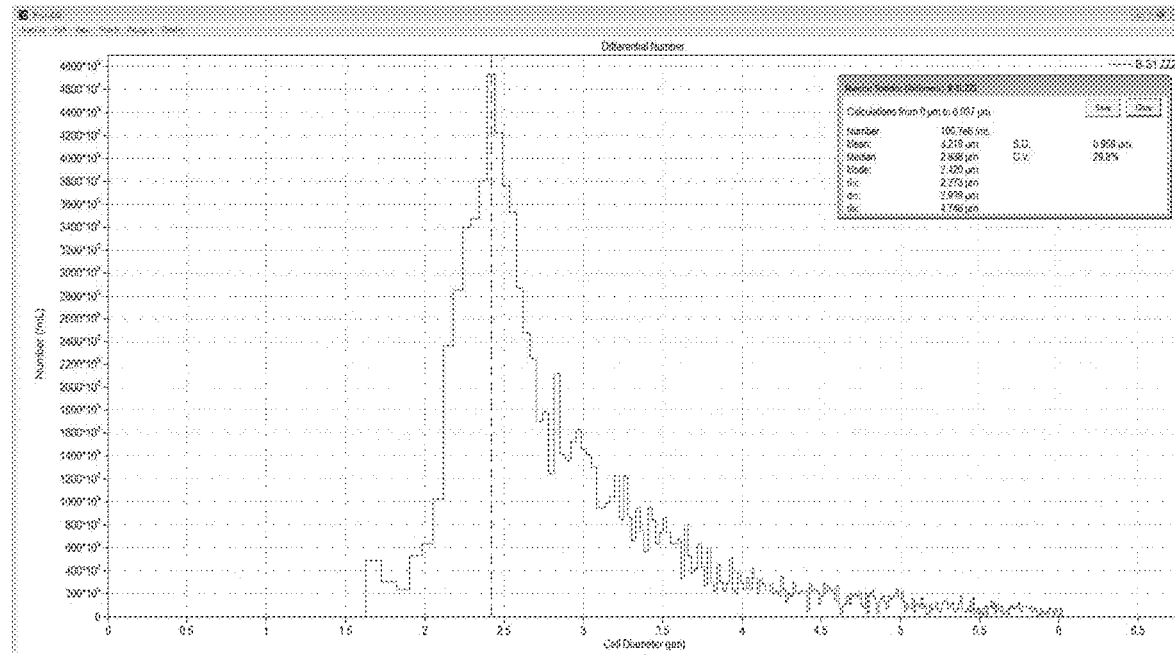
Figure 16H:
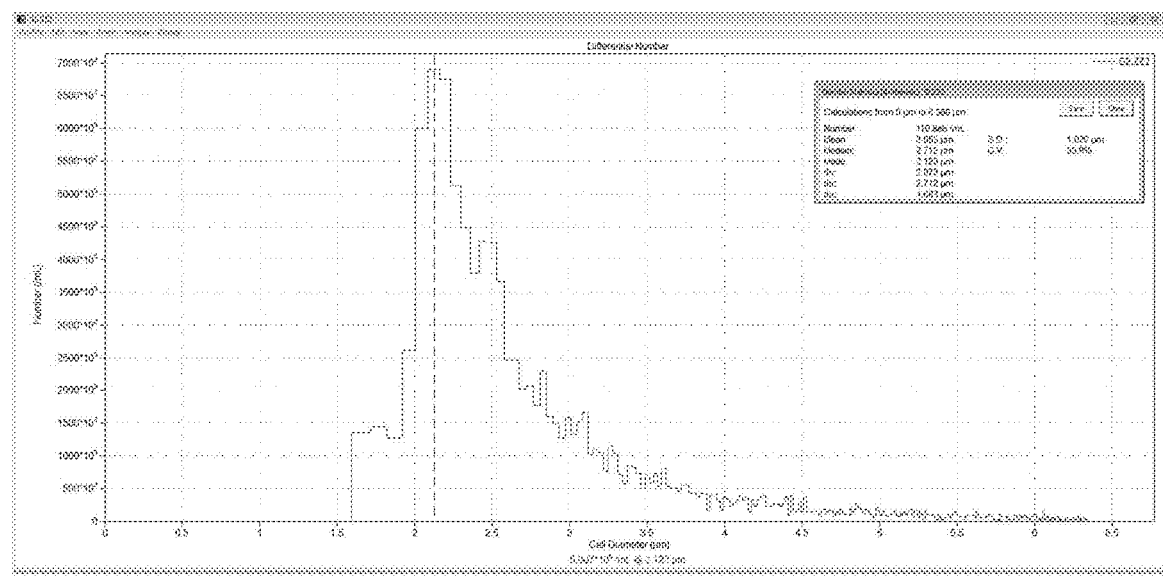
Figure 16I:
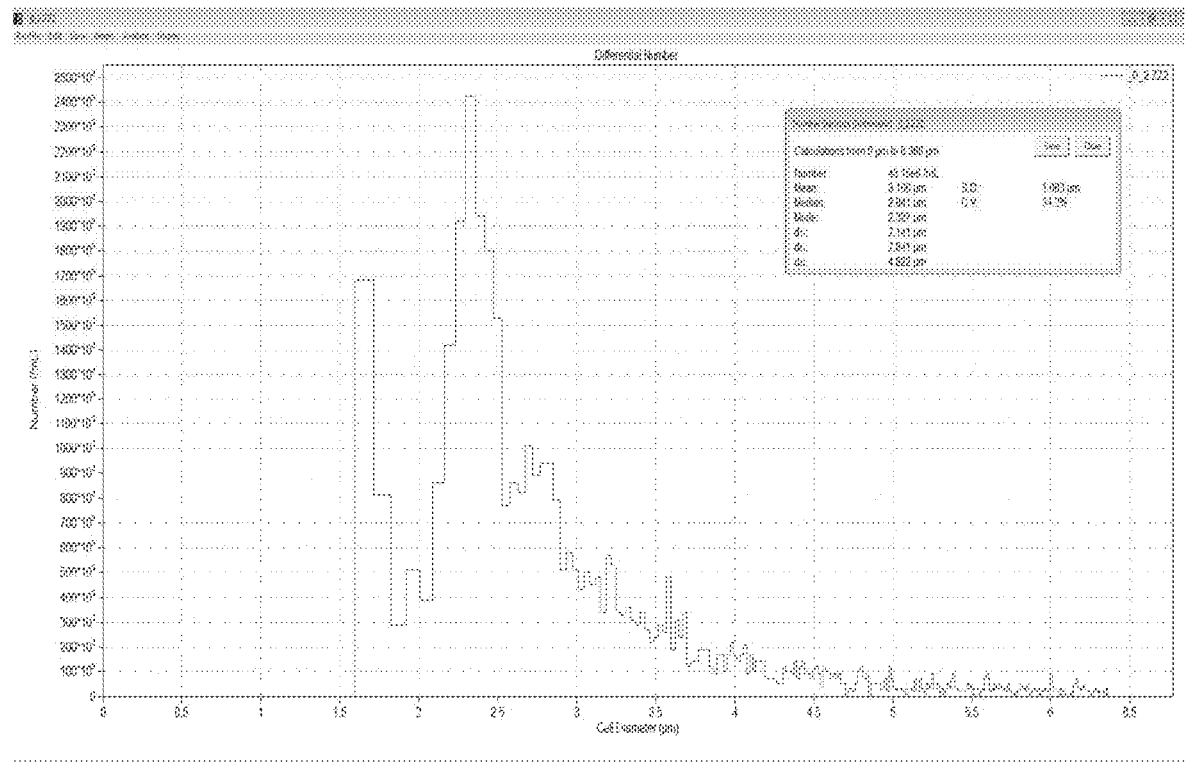
Figure 16J:
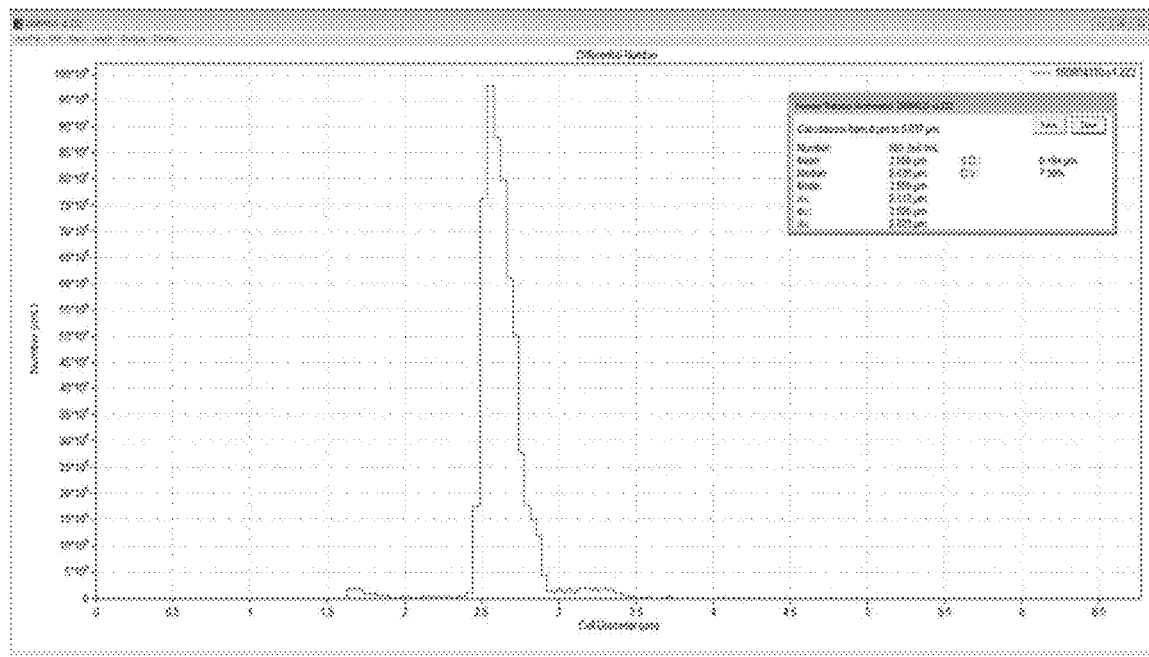

First QCP was aimed to determine the Streptavidin density or surface binding capacity of the loaded beads.13 This protocol was used to compare a batch of Dynbeads® which claimed to have the certain loading capacity. FIG. 16A, FIG. 16B illustrate the chemical structure of Biotin-Fluorescein used in this QCP and way of binding with streptavidin respectively.

FIG. 16A shows a chemical structure of Biot-FAM.

FIG. 16B shows a way of binding between Biot-FAM with Streptavidin.

In the procedure, a 1/251 dilution of Biotin-Fluorescein conjugate of 5 mg/ml in DMSO with 10 mM Phosphate Buffer Saline (PBS) with 0.05% Tween 20 was made. 100␣, of this diluted Biotin-Fluorescein solution was added to 100␣, of suspended Streptavidin Beads 1% w/v, and vortex at room temperature for 30 min. Meanwhile, the Controls were prepared at the same time by adding 100␣ of diluted Biotin-FAM to 100␣ of 10 mM Phosphate Buffer Saline (PBS) with 0.05% Tween 20. After 30 min incubation, the Samples and Controls were placed in the DynaMag-2 Magnetic separator. 150␣, of each tube were transferred to cuvettes for measurement of changes of A495.

Based on the QCP-00194-F1, the following batches were determined and the results were reported as following:

| Document Number: QCP-00194-F2 | | | | Document Revision: 01 | | | |
|---|---|---|---|---|---|---|---|
| Test Date: 21 Mar. 2017 | | | | Release Date: DDMMMYYYY | | | |
| Operator: Omid Khakshoor | | | | QC ID: S000008445 | | | |

| Tested Reagents Info |
|---|

| Description | Part Number | Lot Number | DOE | | | | |
|---|---|---|---|---|---|---|---|
| Streptavidin-conjugated Beads, 1% w/v Stock | 03-01116 | S000008445 | 12 Jun. 2017 | | | | |

| | Abs @ 495 nm | | | Δ abs @ | µg/mL, Biotin- | nmol/mg Biotin- | | |
|---|---|---|---|---|---|---|---|---|
| Sample name | 1 | 2 | Average | 495 nm | Fluorescein | Fluorescein | % CV | Pass/Fail |
| CONTROL | 0.7640 | 0.7680 | 0.7660 | | | | | |
| SAMPLE | 0.5800 | 0.5780 | 0.5790 | 0.1870 | 1.789 | 0.488 | 0.24% | PASS |

| Document Number: QCP-00194-F2 | | | | Document Revision: 01 | | | |
|---|---|---|---|---|---|---|---|
| Test Date: 21 Mar. 2017 | | | | Release Date: DDMMMYYYY | | | |
| Operator: Omid Khakshoor | | | | QC ID: S000008446 | | | |

| Tested Reagents Info |
|---|

| Description | Part Number | Lot Number | DOE | | | | |
|---|---|---|---|---|---|---|---|
| Streptavidin-conjugated Beads, 1% w/v Stock | 03-01116 | S000008446 | 12 Jun. 2017 | | | | |

| | Abs @ 495 nm | | | Δ abs @ | µg/mL, Biotin- | nmol/mg Biotin- | | |
|---|---|---|---|---|---|---|---|---|
| Sample name | 1 | 2 | Average | 495 nm | Fluorescein | Fluorescein | % CV | Pass/Fail |
| CONTROL | 0.7640 | 0.7680 | 0.7660 | | | | | |
| SAMPLE | 0.5150 | 0.5100 | 0.5125 | 0.2535 | 2.425 | 0.662 | 0.69% | PASS |

| Document Number: QCP-00194-F2 | | | | Document Revision: 01 | | | |
|---|---|---|---|---|---|---|---|
| Test Date: 21 Mar. 2017 | | | | Release Date: DDMMMYYYY | | | |
| Operator: Omid Khakshoor | | | | QC ID: S000008447 | | | |

| Tested Reagents Info |
|---|

| Description | Part Number | Lot Number | DOE | | | | |
|---|---|---|---|---|---|---|---|
| Streptavidin-conjugated Beads, 1% w/v Stock | 03-01116 | S000008447 | 12 Jun. 2017 | | | | |

| | Abs @ 495 nm | | | Δ abs @ | µg/mL, Biotin- | nmol/mg Biotin- | | |
|---|---|---|---|---|---|---|---|---|
| Sample name | 1 | 2 | Average | 495 nm | Fluorescein | Fluorescein | % CV | Pass/Fail |
| CONTROL | 0.7640 | 0.7680 | 0.7660 | | | | | |
| SAMPLE | 0.5640 | 0.5630 | 0.5635 | 0.2025 | 1.937 | 0.529 | 0.13% | PASS |

| Document Number: QCP-00194-F2 | | | | Document Revision: 01 | | | |
|---|---|---|---|---|---|---|---|
| Test Date: 31 MAR. 2017 | | | | Release Date: DDMMMYYYY | | | |
| Operator: Omid K | | | | QC ID: S000008475 | | | |

-continued

| Tested Reagents Info | | | | | | | |
|---|---|---|---|---|---|---|---|
| Description | | Part Number | Lot Number | DOE | | | |
| Streptavidin-conjugated Beads, 1% w/v Stock | | 03-01116 | s000008475 | 23 Jun. 2017 | | | |

| | Abs @ 495 nm | | | Δ abs @ | µg/mL, Biotin- | nmol/mg Biotin- | | |
|---|---|---|---|---|---|---|---|---|
| Sample name | 1 | 2 | Average | 495 nm | Fluorescein | Fluorescein | % CV | Pass/Fail |
| CONTROL | 0.7205 | 0.7260 | 0.7233 | | | | | |
| SAMPLE | 0.4760 | 0.4770 | 0.4765 | 0.2468 | 2.361 | 0.644 | 0.15% | PASS |

Document Number: QCP-00194-F2  Document Revision: 01
Test Date: 3 Apr. 2017  Release Date: DDMMMYYYY
Operator: Alex Lee  QC ID: S000008482

| Tested Reagents Info | | | | | | | |
|---|---|---|---|---|---|---|---|
| Description | | Part Number | Lot Number | DOE | | | |
| Streptavidin-conjugated Beads, 1% w/v Stock | | 03-01116 | s000008482 | 26 Jun. 2017 | | | |

| | Abs @ 495 nm | | | Δabs @ | µg/mL, Biotin- | nmol/mg Biotin- | | |
|---|---|---|---|---|---|---|---|---|
| Sample name | 1 | 2 | Average | 495 nm | Fluorescein | Fluorescein | % CV | Pass/Fail |
| CONTROL | 0.7205 | 0.7295 | 0.7250 | | | | | |
| SAMPLE | 0.5010 | 0.5105 | 0.5058 | 0.2193 | 2.097 | 0.572 | 1.33% | PASS |

Besides on those batches with L/N above, during process re-development, couples of batches were tested on Biotin loading and compared with a lot of Dynabeads® M280 SA (L/N 160804110) beads as below:

| | Abs @ 495 nm | | | Δ abs @ | µg/mL, Biotin- | nmol/mg Biotin- |
|---|---|---|---|---|---|---|
| Sample name | 1 | 2 | avg | 495 nm | Fluorescein | Fluorescein |
| CONTROL | 0.7580 | 0.7500 | 0.7540 | | | |
| 06mar2017-A | 0.4850 | 0.4920 | 0.4885 | 0.2655 | 2.540 | 0.693 |
| 06mar2017-B | 0.5320 | 0.5340 | 0.5330 | 0.2210 | 2.114 | 0.577 |
| Dynabead 160804110 | 0.59 | 0.584 | 0.5870 | 0.1670 | 1.598 | 0.436 |
| CONTROL | 0.6970 | 0.7010 | 0.6990 | | | |
| 2-Mar | 0.4360 | 0.4580 | 0.4470 | 0.2520 | 2.411 | 0.658 |

In-house developed Streptavidin conjugated beads with Biotin loading ranged from 488 to 693 pmol/mg. Every batch synthesized here is still larger than Dynabeads® M280 SA (L/N 160804110) 436 pmol/mg. Specification of Dynabeads® this lot numbers was tested as 756 pmol/mg with 14 C conjugated Biotin and Dynabeads® tested different lots could ranged from 650-900 pmol/mg. When comparing the figures, the in-house beads are very close to the range of variable with Dynabeads® M280, SA conjugated, and with a higher loading of biotin/Streptavidin surface for every batches synthesized so far.

QC pass/fail criteria was set as any loading between 450-700 pmol/mg and % CV less than 5% as PASS.

Another QCP-00202-F1 developed at Theranos for the in-house Streptavidin conjugated beads is using Beckman Coulter Z2 Particle Counter with 50 µm aperture to determine the size and distribution.14 At first, 10 mL of Electrolyte solution was dispensed to 15 mL Falcon tubes. 100 µl of Sample beads in 1% w/v was added and mixed well with the Electrolyte solution. Then, 1 mL of the diluted beads solution was transferred to a 10 mL of Electrolyte solution in Accuvate vials. These series of dilution ended up as 1000 fold dilution of 1% w/v beads. QC pass/fail criteria was set as any sizes between 2.4 to 3.3 µm and % CV less than 13% as PASS. FIGS. 16C-16J show results from batches prepared here for sizing quality control (QC).

Dynabeads® M280 SA (L/N 160804110)

DESCRIPTION

Figure 17:
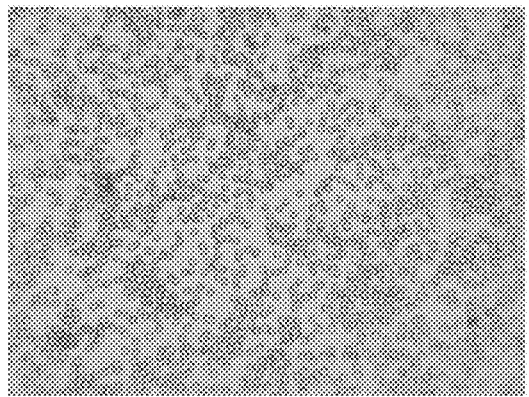
FIG. 17 shows images of in-house PS seeds.
Figure 17:
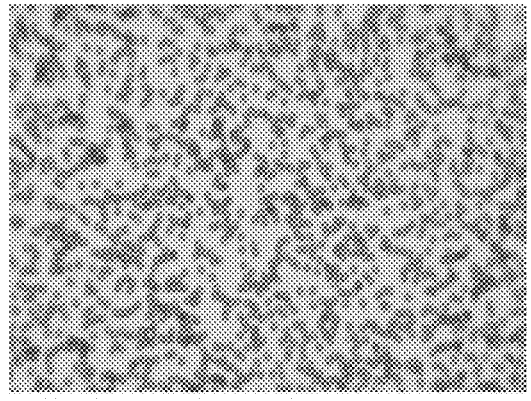

P/N 02-00405 One embodiment of Polystyrene Core Seeds has been successfully developed in-house using carefully controlled and optimized condition for AIBN radical polymerization from styrene monomer, with catalytic amount of polyacrylic acid PAC and water in ethanol solution. This development can deliver monodispersed, uniform spherical beads with size controllable. Result are promising and able to compare with Gold Standard from Industry-Dynabeads®. FIG. 17 showing the microscopic image of the Seeds and Dynabeads reference (800×).

FIG. 17 shows in-house PS seeds (left), Dynabeads M280, sized ~2.8 µm with SA surface (right).

Figure 18:
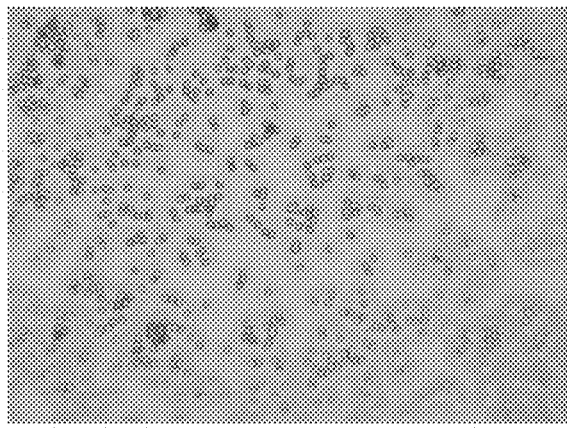
FIG. 18 shows images of in-house PS-PGMA coated seeds (left), co-polymerization formed PS-PGMA beads (right).
Figure 18:
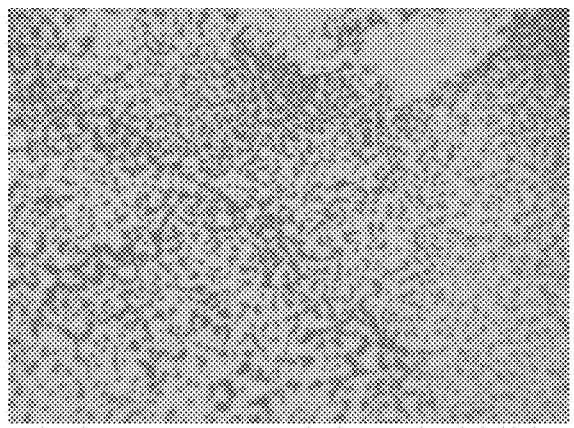

P/N 02-00406 One embodiment of Coated Seeds has been developed with PGMA coating on top of the PS seeds formed from last step. This process is unique and well controlled. PGMA coating allow the same method to be employed on wide range of seeds sizes without compromising the quality and redevelop on other conditions. This step was chosen because other attempts demonstrated co-polymerization of St, DVB, GMA could not easily yield monodispersed beads. With coating method on the seeds surface, this solve both issues of sizes monodisperse control and functional surface introduction by single step. Moreover, this step allows quick in-process checking for well completion of PGMA coating. If the amine surface of next step could not dispense well in aqueous, it would stop the process moving forward. FIG. 18 showing difference of Successful seeds coating and co-polymerization images.

FIG. 18 shows one embodiment of in-house PS-PGMA coated seeds (left), co-polymerization formed PS-PGMA beads (right).

P/N 02-00407 One embodiment has been developed with simple mixing of PGMA coated seeds with excess of ethylene diamine. This step increase the hydrophilic property of the beads surface and served as the in-process QC step for PGMA coating completion. If the beads could not disperse well in aqueous, which formed foaming mixture and indicated the coating step went wrong. This mixture could not continue for next step because of the mixing issue. In most cases, the microscopic image can tell the difference. (FIG. 19)

Figure 19:
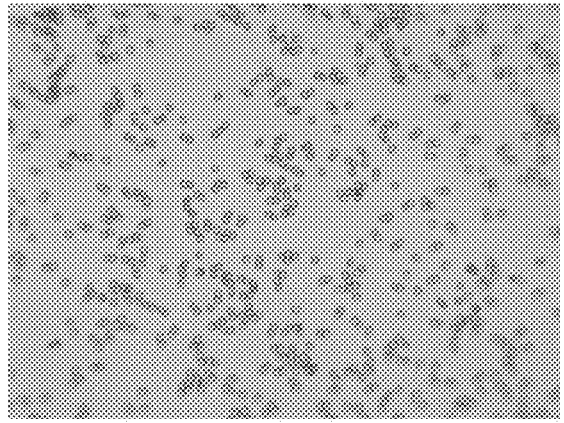
FIG. 19 shows in-house aminated beads.
Figure 19:
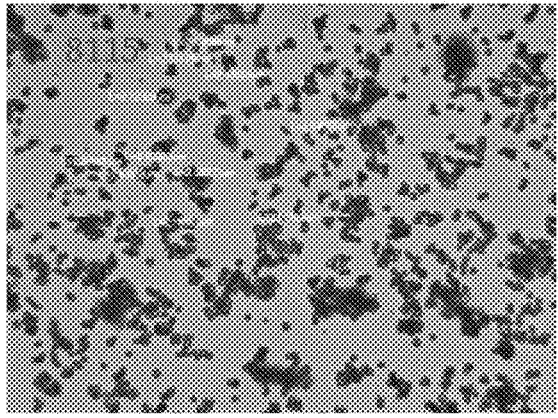

FIG. 19 shows one embodiment of in-house aminated beads (left), aminated beads with incomplete PGMA coating in previous step (right).

Figure 20:
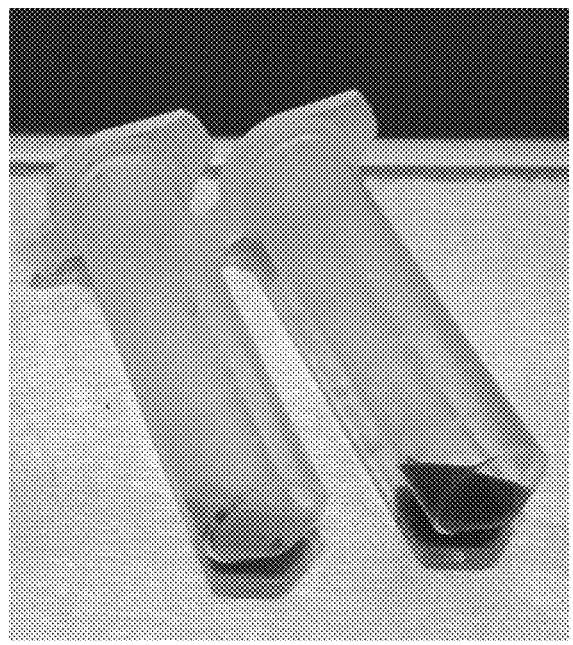
FIG. 20 shows in-house Fe3O4 beads

P/N 02-00408 One embodiment of Iron (II, III) oxide incorporated beads has been prepared based on optimized condition developed at Theranos. This precipitation was selected instead of swelling entrapping method mentioned above because of the controllable loading and less DVB needed for crosslinking. Also, swelling method was not able to perform the high loading of Fe content compare to the current incorporation with precipitation. FIG. 20 records the color or Iron content difference between 2 mentioned methods. Less color means less Iron incorporate and the magnetic responds are much slower in same magnetic field.

FIG. 20 shows one embodiment of in-house Fe3O4 beads with swelling-entrapping (left), in-house beads with precipitation to incorporate Fe3O4 (right).

P/N 02-00426 One embodiment of Aldehyde Surface Activated beads were developed for the quick conjugation of protein free amine or lysine side chain to surface aldehyde. This intermediate was done by suspending Iron (II, III) oxide incorporated beads in excess of glutaraldehyde 50% in water. This step was planned to be happened immediately before the Streptavidin conjugation to avoid any degrading of activity of aldehyde for conjugation. No drying of the product beads is needed although it is okay to dry and stored for months.

P/N 03-01116 One embodiment of Streptavidin conjugated beads finally deliver as 1% w/v formulation with 0.02% NaN3 added as antimicrobial. Conjugation of Streptavidin or other proteins antibodies could be possible too. This step was designed for un-trained workers, as a result, the operation is as simple as 1-2-3. First add the right amount of excess of streptavidin into the aldehyde surface beads which is highly activated towards amines from protein lysine side chains, yet stable. Second, waits for 1-2 hr, then blocking with BSA. Thirdly, cleaning with magnetic separation or centrifuge with deionized water washings.

By way of non-limiting example, all of the six steps designed and developed for this beads project could deliver a well sized, uniform and monodisperse microparticles perform similar to Dynabeads®. Intermediates could be served as individual products for other application. Such as P/N 02-00408, amine surface Iron (II, III) oxide incorporate beads can be used to react with succinimde activated antibodies, antigens for coating. And P/N 02-00426 aldehyde surface activated beads could be react with proteins A/G for suitable antibodies purification applications. They implement the design idea of Modular, and benefits the shorter design cycles and effectiveness in resources saving.

Figure 21:
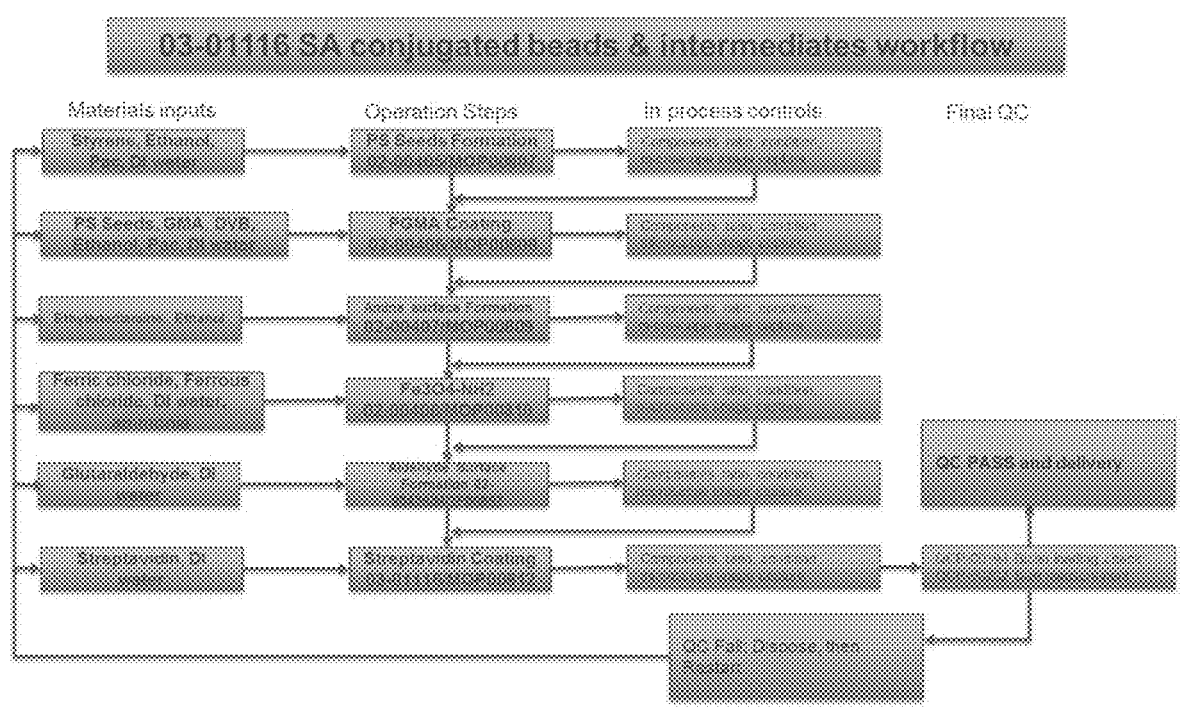
FIG. 21 shows one embodiment of the process of Streptavidin conjugated beads and its intermediates preparation.

The Flow chart in FIG. 21 summarizes one embodiment of the process of Streptavidin conjugated beads and its intermediates preparation:

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood that although whole blood may be the sample used, other types of sample such as saliva, mucus, etc. . . . may also be used.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc . . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. U.S. Provisional Application Ser. No. 62/577, 680 filed Oct. 26, 2017 is fully incorporated herein by reference for all purposes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A method of forming microparticles comprising:
providing a plurality of polystyrene micron particles;
coating each of the polystyrene micron particles with an epoxy layer;
forming an amine surface on the epoxy layer;
suspending the polystyrene micron particles having the amine surface in an aqueous solution to provide a particle suspension;
adding the particle suspension into a dissolved ferric and ferrous chloride solution;
allowing the ferric and ferrous chloride from the solution to penetrate inside the polystyrene micron particles using the amine surface hydrophilicity; and
precipitating the ferric and ferrous ions inside the particles using ammonia; and
wherein the method steps are carried out without using toluene.

2. A method of forming microparticles comprising:
providing a plurality of polystyrene micron particles;
coating each of the polystyrene micron particles with an epoxy layer;
forming an amine surface on the epoxy layer;
suspending the polystyrene micron particles having the amine surface in an aqueous solution to provide a particle suspension;
adding the particle suspension into a dissolved ferric and ferrous chloride solution;
allowing the ferric and ferrous chloride from the solution to penetrate inside the polystyrene micron particles using the amine surface hydrophilicity;
precipitating the ferric and ferrous ions inside the particles using ammonia;
forming an aldehyde activated surface on the amine surface; and
reacting the aldehyde activated surface with protein lysine side chain to form streptavidin conjugated beads; and
wherein the method steps are carried out without using toluene.

3. A method of forming microparticles comprising:
providing a plurality of polystyrene micron particles;
coating each of the polystyrene micron particles with an epoxy layer;
forming an amine surface on the epoxy layer;
suspending the polystyrene micron particles having the amine surface in an aqueous solution to provide a particle suspension;
adding the particle suspension into a dissolved ferric and ferrous chloride solution;
allowing the ferric and ferrous chloride from the solution to penetrate inside the polystyrene micron particles using the amine surface hydrophilicity; and
precipitating the ferric and ferrous ions inside the particles using ammonia;
forming an aldehyde activated surface on the amine surface without drying the polystyrene micron particles after forming said precipitate therein; and
wherein the method steps are carried out without using toluene.

* * * * *